US011185501B2

(12) United States Patent
McDevitt et al.

(10) Patent No.: US 11,185,501 B2
(45) Date of Patent: Nov. 30, 2021

(54) METHOD AND COMPOSITION FOR TARGETED DELIVERY OF THERAPEUTIC AGENTS

(71) Applicant: MEMORIAL SLOAN KETTERING CANCER CENTER, New York, NY (US)

(72) Inventors: Michael R. McDevitt, Bronx, NY (US); Simone Alidori, New York, NY (US); Nima Akhavein, Philadelphia, PA (US); David A. Scheinberg, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 0 days.

(21) Appl. No.: 16/599,978

(22) Filed: Oct. 11, 2019

(65) Prior Publication Data
US 2020/0237663 A1 Jul. 30, 2020

Related U.S. Application Data

(63) Continuation of application No. 15/328,348, filed as application No. PCT/US2015/041756 on Jul. 23, 2015, now abandoned.

(60) Provisional application No. 62/028,615, filed on Jul. 24, 2014.

(51) Int. Cl.
*A61K 9/00* (2006.01)
*A61K 31/711* (2006.01)
*A61K 31/7105* (2006.01)
*A61K 31/713* (2006.01)
*A61K 51/12* (2006.01)
*A61K 47/69* (2017.01)
*A61K 47/52* (2017.01)
*C12N 15/113* (2010.01)

(52) U.S. Cl.
CPC .......... *A61K 9/0092* (2013.01); *A61K 9/0019* (2013.01); *A61K 31/711* (2013.01); *A61K 31/713* (2013.01); *A61K 31/7105* (2013.01); *A61K 47/52* (2017.08); *A61K 47/6925* (2017.08); *A61K 47/6929* (2017.08); *A61K 51/1248* (2013.01); *C12N 15/113* (2013.01); *C12N 15/1135* (2013.01); *C12N 15/1137* (2013.01); *C12N 2310/14* (2013.01); *C12N 2310/351* (2013.01); *C12N 2320/32* (2013.01)

(58) Field of Classification Search
CPC .............. A61K 31/713; A61K 47/6929; A61K 51/1248; C12N 15/113; C12N 15/1135; C12N 15/1137; C12N 2310/14; C12N 2310/351; C12N 2310/32
USPC ........ 424/9.1; 435/6.1, 91.1, 91.31, 45, 458; 514/44 A; 536/23.1, 24.5
See application file for complete search history.

(56) References Cited

U.S. PATENT DOCUMENTS

| 7,858,648 | B2 | 12/2010 | Bianco et al. |
| 8,540,965 | B2 | 9/2013 | Scheinberg et al. |
| 9,629,927 | B2 | 4/2017 | Scheinberg et al. |
| 2007/0228317 | A1 | 10/2007 | Barrera et al. |
| 2008/0193490 | A1 | 8/2008 | Hirsch et al. |
| 2011/0166201 | A1 | 7/2011 | Ju et al. |
| 2016/0237157 | A1 | 8/2016 | Dennis et al. |
| 2017/0173177 | A1* | 6/2017 | Bangera ............. A61K 38/1732 |

OTHER PUBLICATIONS

Molitoris et al J. Am. Soc. Nephrol., vol. 20, pp. 1754-1764 (2009) (Year: 2009).*
Bylander et al Am. J. Physiol. Renal Physiol. vol. 294, pp. F480-F490 (2008) (Year: 2008).*
Fujino et al Am. J. Physiol. Renal Physiol., vol. 305, pp. F1617-F1627 (2013) (Year: 2013).*
Ladeira et al Nanotechnology, vol. 21, 305101, pp. 1-12 (2010) (Year: 2010).*
McCarroll et al Bioconj. Chem., vol. 21, pp. 56-63 (2010) (Year: 2010).*
Ruggiero et al: "Paradoxical glomerular filtration of carbon nanotubes", Proceedings National Academy of Sciences PNAS, vol. 107, No. 27, Jul. 6, 2010 (Jul. 6, 2010), pp. 12369-12374, XP055453252, US, ISSN: 0027-8424, DOI: 10.1073/pnas.0913667107.
Alidori, et al., "Deploying RNA and DNA with Functionalized Carbon Nanotubes," The Journal of Physical Chemistry, C Nanomater Interfaces, Mar. 2013, pp. 5982-5992, vol. 117, No. 11.
B. A. Molitoris et al: "siRNA Targeted to p53 Attenuates Ischemic and Cisplatin-Induced Acute Kidney Injury", Journal of the American Society of Nephrology, vol. 20, No. 8, May 21, 2009 (May 21, 2009), pp. 1754-1764, XP055205502, ISSN: 1046-6673, DOI: 10.1681/ASN.2008111204 *abstract*.
Devarajan, et al., "Proteomics for Biomarker Discovery in Acute Kidney Injury," Semin Nephrol, Nov. 2007, pp. 637-651, vol. 27, No. 6.
Discipio R G et al: "C5a mediates secretion and activation of matrix metalloproteinase 9 from human eosinophils and neutrophils", International Immunopharmacology, Elsevier, Amsterdam, NL, vol. 6, No. 7, Jul. 1, 2006 (Jul. 1, 2006), pp. 1109-1118, XP024976867, ISSN: 1567-5769, DOI: 10.1016/J.INTIMP.2006.02.006 [retrieved on Jul. 1, 2006] *the whole document*.

(Continued)

*Primary Examiner* — Jane J Zara
(74) *Attorney, Agent, or Firm* — Foley & Lardner LLP

(57) ABSTRACT

Functionalized single walled or multi-walled carbon nanotubes (f-CNTs) can be delivered into mammals to targeted organs, such as the kidney and the liver. These f-CNTs may be non-covalently linked or covalently linked to therapeutic agents. In particular, the application delivers carbon nanotube-therapeutic agent conjugates to a target organ, thereby preventing or reducing damages to the organ caused by other agents or procedure.

6 Claims, 15 Drawing Sheets

Specification includes a Sequence Listing.

(56) References Cited

OTHER PUBLICATIONS

Elimelda Moige Ongeri et al: "Villin and actin in the mouse kidney brush-border membrane bind to and are degraded by meprins, an interaction that contributes to injury in ischemia-reperfusion", American Journal of Physiology—Renal Physiology, Oct. 1, 2011(Oct. 1, 2011), pp. 871-882, XP055480910, United States DOI: 10.1152/ajprenal.00703.2010 *the whole document*.

Fujino, et al., "Silencing of p53 RNA through transarterial delivery ameliorates renal tubular injury and downregulates GSK-3 beta expression after ischemia-reperfusion injury," American Journal of Renal Physiology, Dec. 1, 2013, pp. F1617-F1627, vol. 305, No. 11.

Georgakilas, et al., "Organic functionalization of carbon nanotubes," ChemComm, 2002, pp. 3050-3051.

Hamar P et al: "Small Interfering RNA Targeting Fas Protects Mice Against Renal Ischemia-Reperfusion Injury", Proceedings National Academy of Sciences PNAS, National Academy of Sciences, US, vol. 101, No. 41, Oct. 12, 2004 (Oct. 12, 2004), pp. 14883-14888, XP003008314, ISSN: 0027-8424, DOI: 10.1073/PNAS.0406421101 *abstract*.

Hamar, et al., "Small Interfering RNA Targeting Fas Protects Mice Against Renal Ischemia-Reperfusion Injury," Proceedings National Academy of Sciences, Oct. 12, 2004, pp. 14883-14888, vol. 101, No. 41.

Hefner, et al., "Increased potency and longevity of gene silencing using validated Dicer substrates," Journal of Biomolecular Techniques, Sep. 2008, pp. 231-237, vol. 19, No. 4.

Kuwahaka et al: "Delivery or siRNA into tne blood-brain carrier: recent advances and future perspective", Therapeutic Delivery, vol. 3, No. 4, Apr. 1, 2012 (Apr. 1, 2012), pp. 417-420, XP055202700, ISSN: 2041-5990, DOI: 10.4155/tde.12.22.

International Search Report and Written Opinion in International Application No. PCT/US2015/041756 dated Oct. 29, 2015 (9 pages).

Bylander et al: "Targeted disruption of the meprin metalloproteinase [beta] gene protects against renal ischemia-reperfusion injury in mice", American Journal of Physiology: Renal Physiology, vol. 294, No. 3, Mar. 1, 2008 (Mar. 1, 2008), pp. F480-F490, XP055480914, United States ISSN: 1931-857X, DOI: 10.1152/ajprenal.00214.2007 *the whole document*.

McCarroll et al: "Nanotubes Functionalized with Lipids and Natural Amino Acid Dendrimers: A New Strategy to Create Nanomaterials for Delivering Systemic RNAi", Bioconjugate Chemistry, vol. 21, No. 1, Jan. 20, 2010 (Jan. 20, 2010), pp. 56-63, XP055014548, ISSN: 1043-1802, DOI: 10.1021/bc900296z *the whole document* *abstract*.

Ladeira M S et al: "Highly efficient siRNA delivery system into human and murine cells using single-wall carbon nanotubes," Nanotechnology IOP, Bristol, GB, vol. 21, No. 38, Aug. 27, 2010 (Aug. 27, 2010), p. 385101, XP020197445, ISSN: 0957-4484, DOI: 10.1088/0957-4484/21/38/385101 *the whole document*.

Li X et al: "Allevation of ischemia-reperfusion injury in rat liver transplantation by induction of small interference RNA targeting Fas", Langenbeck's Archives of Surgery, Springer, Berlin, DE, vol. 392, No. 3, Jan. 19, 2007 (Jan. 19, 2007), pp. 345-351, XP019517373, ISSN: 1435-2541, DOI: 10.1007/S00423-006-0142-5 *the whole document*.

Li, et al., "Alleviation of ischemia-reperfusion injury in rat liver transplantation by induction of small interference RNA targeting Fas," Langenbeck's Archives of Surgery, Jan. 19, 2007, pp. 345-351, vol. 392, No. 3, Springer, Berlin, Germany.

McCarroll, et al., "Nanotubes Functionalized with Lipids and Natural Amino Acid Dendrimers: A New Strategy to Create Nanomaterials for Delivering Systemic RNAi," Bioconjugate Chemistry, Jan. 20, 2010, pp. 56-63, vol. 21, No. 1.

McDevitt, et al., "PET Imaging of Soluble Yttrium-86-Labeled Carbon Nanotubes in Mice," PLoS one, Sep. 2007, pp. 1-10, Issue 9.

McDevitt, et al., "Tumor Targeting with Antibody-Functionalized, Radiolabeled Carbon Nanotubes," The Journal of Nuclear Medicine, Jul. 2007, pp. 1180-1189, vol. 48, No. 7.

Mulvey, et al., "Self-assembly of carbon nanotubes and antibodies on tumours for targeted amplified delivery," Nature Nanotechnology, Oct. 2013, pp. 763-771, vol. 8, No. 10.

Nadine Wong Shi Kam et al: "Functionalized of Carbon Nanotubes via Cleavable Disulfide Bonds for Efficient Intracellular Delivery of siRNA and Potent Gene Silencing", Journal of the American Chemical Society, American Chemical Society, US, vol. 127, No. 36, Jan. 1, 2005 (Jan. 1, 2005), pp. 12492-12493, XP007915883, ISSN: 0002-7863, DOI: 10.1021/JA053962K *the whole document* *Supporting Information*.

Ruggiero, et al., "Imaging and treating tumor vasculature with targeted radiolabeled carbon nanotubes," International Journal of Nanomedicine, 2010, pp. 783-802, vol. 5.

Ruggiero, et al., "Paradoxical glomerular filtration of carbon nanotubes," PNAS, Jul. 6, 2010, pp. 12369-12374, vol. 107, No. 27.

Scheinberg, et al., "Carbon Nanotubes," Drug Delivery in Oncology: From Basic Research to Cancer Therapy, 2011, pp. 1163-1185, vol. 3, Wiley-VCH, Weinheim, Germany.

Schindelin, et al., "Fiji—an open source platform for biological image analysis," Nature Methods, 2012, pp. 676-682, vol. 9, No. 7.

Simone Alidori et al: "Targeted fibrillar nanocarbon RNAi treatment of acute kidney injury", Science Translational Medicine, vol. 8, No. 331, Mar. 23, 2016 (Mar. 23, 2016), pp. 331ra39-331ra39, XP055453103, US, ISSN: 1946-6234, DOI: 10.1126/scitranslmed.aac9647 *the whole document*.

Singh, et al., "Polyamine functionalized carbon nanotubes: synthesis, characterization, cytotoxicity and siRNA binding," Journal of Materials Chemistry, 2011, pp. 4850-4860, vol. 21.

T. Fujino et al: "Silencing of p53 RNA through transarterial delivery ameliorates renal tubular injury and downregulates GSK-3? expression after ischemia-reperfusion injury", American Journal of Physiology. Renal Physiology, Dec. 1, 2013 (Dec. 1, 2013), pp. F1617-F1627, XP055205505, ISSN: 1931-857X, DOI: 10.1152/ajprenal.00279.2013 abstract* *the whole document*.

Villa, et al., "Synthesis and biodistribution of oligonucleotide-functionalized, tumor-targetable carbon nanotubes," Nano Letters, Dec. 2008, pp. 4221-4228, vol. 8, No. 12.

Wong, et al., "Functionalization of Carbon Nanotubes via Cleavable Disulfide Bonds for Efficient Intracellular Delivery of siRNA and Potent Gene silencing," Journal of the American Chemical Society, Jan. 1, 2005, pp. 12492-12493, vol. 127, No. 36.

Zheng et al: "Attenuating Ischemia-Reperfusion Injury in Kidney Transplantation by Perfusing Donor Organs With siRNA Cocktail Solution :", Transplantation, vol. 100, No. 4, Apr. 1, 2016 (Apr. 1, 2016), pp. 743-752, XP055453670, GB, ISSN: 0041-1337, DOI: 10.1097/TP.0000000000000960.

Zheng et al: "Gene Silencing of Complement C5a Receptor Using siRNA for Preventing Ischemia/Reperfusion Injury", American Journal of Pathology., vol. 173, No. 4, Oct. 1, 2008 (Oct. 1, 2008), pp. 973-980, XP055453875, US ISSN: 0002-9440, DOI: 10.2353/ajpath.2008.080103 *the whole document*.

Zheng, et al., "Preventing Renal Ischemia-Reperfusion Injury Using Small Interfering RNA by Targeting Complement 3 Gene," American Journal of Transplantation, Sep. 1, 2006, pp. 2099-2108, vol. 6, No. 9.

Communication pursuant to Article 94(3) EPC issued in corresponding European Patent Application No. 15 823 961.6, dated May 6, 2021.

* cited by examiner

SEQUENCE LISTING

<160> NUMBER OF SEQ ID NOS: 12

<210> SEQ ID NO 1
<211> LENGTH: 24
<212> TYPE: DNA

```
<213> ORGANISM: Artificial Sequence
<220> FEATURE:
<223> OTHER INFORMATION: Synthetic Dicer validated RNA sequence:  siEGFP

<400> SEQUENCE: 1
gcaagcugac ccugaaguuc autt                                            24

<210> SEQ ID NO 2
<211> LENGTH: 24
<212> TYPE: RNA
<213> ORGANISM: Artificial Sequence
<220> FEATURE:
<223> OTHER INFORMATION: Synthetic Dicer validated RNA sequence:  siEGFP

<400> SEQUENCE: 2
augaacuuca gggucagcuu gccg                                            24

<210> SEQ ID NO 3
<211> LENGTH: 24
<212> TYPE: DNA
<213> ORGANISM: Artificial Sequence
<220> FEATURE:
<223> OTHER INFORMATION: Synthetic Dicer validated RNA sequence:  siEGFP
<220> FEATURE:
<221> NAME/KEY: misc_feature
<222> LOCATION: (1)..(1)
<223> OTHER INFORMATION: Amine modified RNA sequence, NH2-(CH2)6- group
      at 5'- end

<400> SEQUENCE: 3
gcaagcugac ccugaaguuc autt                                            24

<210> SEQ ID NO 4
<211> LENGTH: 24
<212> TYPE: DNA
<213> ORGANISM: Artificial Sequence
<220> FEATURE:
<223> OTHER INFORMATION: Synthetic Dicer validated RNA sequence:  siEGFP
<220> FEATURE:
<221> NAME/KEY: misc_feature
<222> LOCATION: (1)..(1)
<223> OTHER INFORMATION: Cyanine 3 succinimidyl ester modified sequence,
      Cy3(CH2)2C(O)NH-(CH2)6- group at 5'- end

<400> SEQUENCE: 4
gcaagcugac ccugaaguuc autt                                            24

<210> SEQ ID NO 5
<211> LENGTH: 25
<212> TYPE: DNA
<213> ORGANISM: Artificial Sequence
<220> FEATURE:
<223> OTHER INFORMATION: Synthetic Dicer validated RNA sequence:
      siScram

<400> SEQUENCE: 5
cguuaaucgc guauaauacg cguat                                           25

<210> SEQ ID NO 6
<211> LENGTH: 27
<212> TYPE: RNA
<213> ORGANISM: Artificial Sequence
<220> FEATURE:
<223> OTHER INFORMATION: Synthetic Dicer validated RNA sequence:
      siScram

<400> SEQUENCE: 6
cagcaauuag cgcauauuau gcgcaua                                         27
```

<210> SEQ ID NO 7
<211> LENGTH: 25
<212> TYPE: DNA
<213> ORGANISM: Artificial Sequence
<220> FEATURE:
<223> OTHER INFORMATION: Synthetic Dicer validated RNA sequence: siCtr1

<400> SEQUENCE: 7
ggcaugaaca ugugaauugc uggtt                                       25

<210> SEQ ID NO 8
<211> LENGTH: 27
<212> TYPE: RNA
<213> ORGANISM: Artificial Sequence
<220> FEATURE:
<223> OTHER INFORMATION: Synthetic Dicer validated RNA sequence: siCtr1

<400> SEQUENCE: 8
aaccagcaau ucacauguuc augccug                                     27

<210> SEQ ID NO 9
<211> LENGTH: 25
<212> TYPE: DNA
<213> ORGANISM: Artificial Sequence
<220> FEATURE:
<223> OTHER INFORMATION: Synthetic Dicer validated RNA sequence:
      siMep1b

<400> SEQUENCE: 9
ggaauugacc aagacauauu ugata                                       25

<210> SEQ ID NO 10
<211> LENGTH: 27
<212> TYPE: RNA
<213> ORGANISM: Artificial Sequence
<220> FEATURE:
<223> OTHER INFORMATION: Synthetic Dicer validated RNA sequence:
      siMep1b

<400> SEQUENCE: 10
uaucaaauau gucuugguca auccuc                                      27

<210> SEQ ID NO 11
<211> LENGTH: 25
<212> TYPE: DNA
<213> ORGANISM: Artificial Sequence
<220> FEATURE:
<223> OTHER INFORMATION: Synthetic Dicer validated RNA sequence:
      siTrp53

<400> SEQUENCE: 11
aggagucaca gucggauauc agcct                                       25

<210> SEQ ID NO 12
<211> LENGTH: 27
<212> TYPE: RNA
<213> ORGANISM: Artificial Sequence
<220> FEATURE:
<223> OTHER INFORMATION: Synthetic Dicer validated RNA sequence:
      siTrp53

<400> SEQUENCE: 12
aggcugauau ccgacuguga cuccucc                                     27

METHOD AND COMPOSITION FOR TARGETED DELIVERY OF THERAPEUTIC AGENTS

CROSS-REFERENCE TO PRIOR APPLICATIONS

This application is a continuation of U.S. patent application Ser. No. 15/328,348, filed Jan. 23, 2017, which is a National Stage Application of PCT/US2015/041756, filed Jul. 23, 2015, which claims the benefit of and priority to U.S. Provisional Patent Application No. 62/028,615, filed on Jul. 24, 2014, the entire contents of which are incorporated herein by reference.

GOVERNMENT SUPPORT

This invention was made with Government support under grant no. DE-SC0002456 awarded by the Department of Energy. The Government has certain rights in the invention.

SEQUENCE LISTING

The instant application contains a Sequence Listing which has been filed electronically in ASCII format and is hereby incorporated by reference in its entirety. Said ASCII copy is named 115872-0336_SL.txt and is 3,288 bytes in size.

FIELD

The present application relates generally to methods for targeted delivery of therapeutic agents and, in particular, to targeted delivery of therapeutic agents to kidney, spleen, and liver tissue with carbon nanotubes.

BACKGROUND

Acute kidney injury (AKI) is described by an abrupt decline in renal function, specifically, an inability to concentrate urine, eliminate nitrogenous waste, and sustain homeostatic fluid levels. Currently there is no FDA-approved pharmaceutical for the prevention or treatment of AKI, which is associated to very high rates of mortality and morbidity of hospitalized patients. The operational definition of AKI includes increased serum creatinine ($\geq 0.3$ mg/dL) and oliguria ($<0.5$ mL/kg/h for more than 6 h). It is a ubiquitous medical condition that is seen in ~7% of hospitalized patients. Many conventional medical treatments and procedures unavoidably produce nephrotoxic and renal ischemic insults and are prominent contributors to renal injury. Nephrotoxic drugs include antibiotics, such as aminoglycosides, sulfonamides, amphotericin B, foscarnet, quionlones (e.g., ciprofloxacin), rifampin, tetracycline, acyclovir, pentamidine, vanomycin; chemotherapeutics and immunosuppressants, such as cisplatin, methotrexate, mitomycin, cyclosporine, ifosphamide, zoledronic acid; antihyperlipidemics, such as statin drugs (rhabdomyolysis) or gemfibrozil; drugs of abuse, such as cocaine, heroin, methamphetamine, or methadone; heavy metals, such as mercury, lead, arsenic, bismuth, or lithium; miscellaneous drugs, such as chronic stimulant laxative use, radiographic contrast, ACE inhibitors, NSAIDs, aspirin, mesalamine (e.g., asacol, pentasa), and aristocholic acid. Ischemic events resulting from surgical procedures or crush accidents also contribute to AKI. AKI is also a common development from sepsis.

There is a high rate of mortality in subjects with AKI. Morbidity is severe and almost half of the elderly AKI-afflicted population will succumb. An increasingly aged population exacerbates the problem because of the decreased ability of this patient subset to recover from renal damage.

The pathogenesis of AKI involves a nephrotoxic, ischemic, or septic insult which results in loss of polarity of the epithelial cell of the kidney with mislocation of adhesion molcules and $Na^+$, $K^+$-ATPase and other proteins. If the insult is severe, there is cell death by either necrosis or apoptosis. In addition, because of the mislocation of adhesion molecules, viable epithelial kidney cells slough off. Desquamated cells and cellular debris can interact with luminal proteins to physically obstruct the tubule lumen. If provided with the correct nutrients and oxygen supply, the kidney can then initiate a repair process. Viable epithelial cells dedifferentiate and migrate to replace the lost cells. These cells may then proliferate so that a normal epithelium is restored to the kidney.

Currently, treatment of AKI is largely supportive and effective preventative therapies are needed. The high rates of morbidity and mortality associated with AKI correlate with protracted, expensive hospital stays. The pathogenesis of AKI has been characterized by the loss of renal epithelial cell polarity, de-differentiation, apoptosis, necrosis, fibrosis, and inflammation following a renal insult. In particular, tubule damage results from renal ischemia and nephrotoxins. Prophylaxis, directed at the PTC, anticipating kidney damage from a prescribed drug therapy or ischemia and reperfusion event must be developed.

SUMMARY

One aspect of the present application relates to a method for preventing or reducing liver and/or kidney injury. The method comprises the steps of administering to a subject in need thereof an effective amount of a pharmaceutical composition comprising (1) one or more therapeutic RNAs conjugated to functionalized carbon nanotubes (f-CNTs) and (2) a pharmaceutically acceptable carrier, wherein said one or more therapeutic RNAs inhibit expression of one or more genes selected from the group consisting of MMP-9, JNK, Epas1, Hif1an, Ac1, Fih1, Irp1, Egln1, Egln2, Egln3, PHD1, PHD2, PHD3, CTR1, CTR2, cFOS, FOS, cJUN, JUN, Fra1, Fra2, ATP, AP-1, MEP1A, MEP1B, VIM, p53, FASR, FASL, COL3A1, Kim-1 and C3 gene.

In some embodiments, the liver and/or kidney injury include injuries caused by hepatic toxins, nephrotoxins and ischemia.

In some embodiments, the one or more therapeutic RNAs are non-covalently linked to the f-CNTs.

In some embodiments, the f-CNTs are functionalized single walled carbon nanotubes (f-SWCNTs), functionalized multi-walled carbon nanotubes (f-MWCNT), or any fibrillar (aspect ratio greater than 1) macromolecule.

In some embodiments, the pharmaceutical composition is prophylactically administered before the occurrence of liver or kidney injury.

In some other embodiments, the pharmaceutical composition is administered after the occurrence of liver or kidney injury.

In some embodiments, the one or more therapeutic RNAs are selected from the group consisting of siRNAs, miRNA precursors, single-stranded mature miRNAs, double-stranded mature miRNAs and antisense RNAs.

Another aspect of the present application relates to a pharmaceutical composition for preventing or reducing liver and/or kidney injury, comprising (1) one or more therapeutic RNAs linked to functionalized carbon nanotubes (f-CNTs) and (2) a pharmaceutically acceptable carrier, wherein the one or more therapeutic RNA inhibit expression of one or more genes selected from the group consisting of MMP-9, JNK, Epas1, Hif1an, Ac1, Fih1, Irp1, Egln1, Egln2, Egln3, PHD1, PHD2, PHD3, CTR1, CTR2, cFOS, FOS, cJUN, JUN, Fra1, Fra2, ATP, AP-1, MEP1A, MEP1B, VIM, p53, FASR, FASL, COL3A1, Kim-1 and C3 gene.

BRIEF DESCRIPTION OF THE DRAWINGS

The above and other objects and advantages of the application will be apparent upon consideration of the following detailed description, taken in conjunction with the accompanying figures.

FIG. 1A is a graphic illustration of the key functional groups that were appended to SWCNT-[([86Y]DOTA)(AF488)(AF680)] (f-CNT) for the dynamic positron emission topography (PET) study. The figure is not drawn to scale and only contain the key appended moieties. FIG. 1B shows time-activity curves generated from region-of-interest analysis (% injected dose (ID)/g (mean±s.d.)) of liver accumulation and blood compartment clearance in four mice that were PET imaged. FIG. 1C shows biodistribution of f-CNT in select tissue and bile (% ID/g (mean±s.d.)) at 1 h post injection.

FIG. 3A shows quantitative ROI analysis of these images described a significant decrease of basal p53 expression in the fCNT/siTrp53 group versus siTrp53 alone ($P<0.0001$) and PBS vehicle ($P<0.0001$). Similar observations were made in the kidney cortices stained for meprin-1β expression. FIG. 3B shows ROI analysis of these images described a significant decrease of basal meprin-1β expression in the fCNT/siMep1b group versus siMep1b alone ($P<0.0001$) and PBS ($P<0.0001$).

FIG. 4A is a Kaplan-Meier plot of the percent survival as a function of time from cisplatin administration showed the effects of each RNAi treatment condition. The groups are as follows: f-CNT/siMep1b; f-CNT/siTrp53; f-CNT/siScram; siMep1b only; siTrp53 only; combination f-CNT/siMep1b/siTrp53 (the uppermost plotline after 10 days post-cisplatin administration); combination siMep1b/siTrp53; and f-CNT/siCtr1. (n.b., These curves were nudged to permit full view of the data lines). FIG. 4B is a Forest plot of the hazard ratios of the various prophylactic control groups versus the combination f-CNT/siMep1b/siTrp53 strongly favored this f-CNT drug combination treatment in minimizing renal injury arising form cisplatin toxicity. FIG. 4C shows analysis of the picrosirius red staining of the combination group, f-CNT/siMep1b/siTrp53, right bars, and of the control f-CNT/siScram group, left bars, after 14 and 180 days from cisplatin administration. No difference was recorded at 14 days between the two groups, whereas the fibrosis level was significantly higher for the f-CNT/siScram group ($p=0.0397$) at 180 days. FIG. 4D shows analysis of the CD3 immunofluorescence of the combination group, fCNT/siMep1b/siTrp53, red bar, and of the control fCNT/siScram group, blue bar, after 14 and 180 days from cisplatin administration. The level of CD3 was significantly lower for the fCNT/siMep1b/siTrp53-treated group at both 14 ($p=0.0007$) and 180 days ($p=0.0006$). FIG. 4E shows analysis of CD45 immunofluorescence of the combination group, f-CNT/siMep1b/siTrp53, right bars, and of the control f-CNT/siScram group, left bars, after 14 and 180 days from cisplatin administration. The level of CD45 was significantly lower for the f-CNT/siMep1b/siTrp53-treated group at both 14 ($p=0.0011$) and 180 days ($p=0.0100$). FIG. 4F shows analysis of the Iba-1 immunofluorescence of the combination group, f-CNT/siMep1b/siTrp53, right bars, and of the control f-CNT/siScram group, left bars, after 14 and 180 days from cisplatin administration. The level of Iba-1 was significantly lower for the f-CNT/siMep1b/siTrp53-treated group at both 14 ($p<0.0001$) and 180 days ($p<0.0001$).

DETAILED DESCRIPTION

Figure 1A:
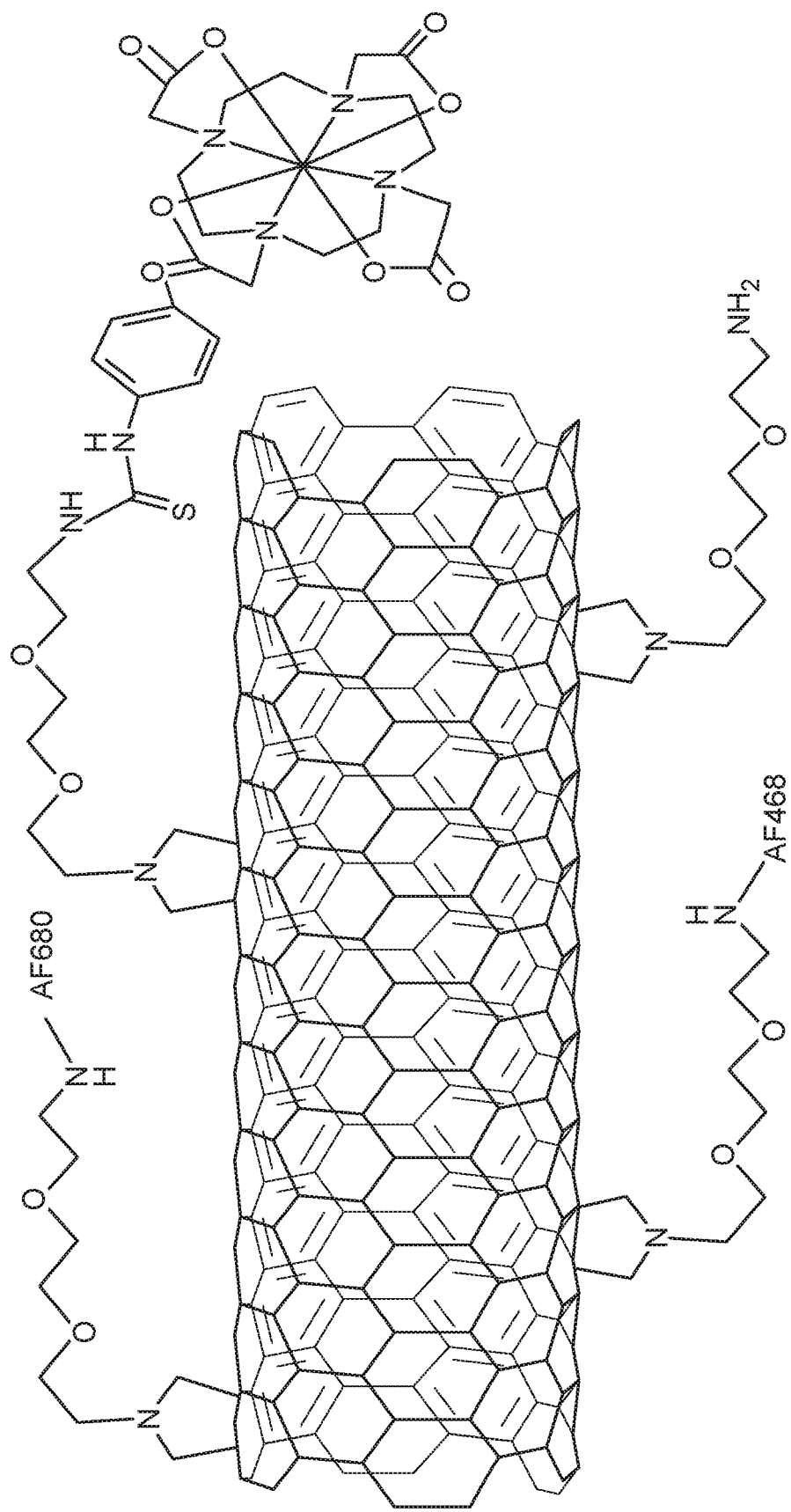
FIGS. 1A-1C show blood clearance and tissue distribution of f-CNT in a mouse model.

Some modes for carrying out the present invention are presented in terms of its exemplary embodiments, herein discussed below. However, the present invention is not limited to the described embodiment and a person skilled in the art will appreciate that many other embodiments of the present invention are possible without deviating from the basic concept of the present invention, and that any such work around will also fall under scope of this application. It is envisioned that other styles and configurations of the present invention can be easily incorporated into the teachings of the present invention, and only one particular configuration shall be shown and described for purposes of clarity and disclosure and not by way of limitation of scope.

Headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). The terms "a" and "an" herein do not denote a limitation of quantity, but rather denote the presence of at least one of the referenced items.

One aspect of the present application relates to a method for preventing or reducing kidney and/or liver injury. The method comprises the steps of administering to a subject in need thereof an effective amount of a pharmaceutical composition comprising (1) one or more therapeutic agents conjugated to functionalized carbon nanotubes (f-CNTs) and (2) a pharmaceutically acceptable carrier, wherein said one or more therapeutic agents inhibit expression of one or more genes selected from the group consisting of MMP-9, JNK, Epas1, Hif1an, Ac1, Fih1, Irp1, Egln1, Egln2, Egln3, PHD1, PHD2, PHD3, CTR1, CTR2, cFOS, FOS, cJUN, JUN, Fra1, Fra2, ATP, AP-1, MEP1A, MEP1B, VIM, p53, FASR, FASL, COL3A1, Kim-1 and C3 gene.

The f-CNT provides a delivery vehicle that can be loaded with the therapeutic agents and specifically directed to the kidney and/or liver bearing the therapeutic cargo. The f-CNT-therapeutic agent conjugates behave like small molecules in vivo and effectively delivers the therapeutic agents to cells in kidney and liver.

Functionalized Carbon Nanotubes

Carbon nanotubes (CNTs) are allotropes of carbon with a cylindrical nanostructure. The carbon atoms are all surface atoms formed in regular structures with defined periodicity. Nanotubes have been constructed with an aspect (length-to-diameter) ratio of up to $10^6$. In some embodiments, the CNTs have an aspect ratio of $10^0$-$10^5$. In some embodiments, the CNTs have about ~8000 carbon atoms per 100 nanometers of length (for a d~1.4 nm). The CNTs of the present application may have metallic or semiconducting properties. In some embodiments, the CNTs of the present application are single-walled CNTs (SWCNTs), functionalized multi-walled carbon nanotubes (f-MWCNT), or any fibrillar (aspect ratio greater than 1) macromolecule.

In some embodiments, the CNTs of the present application are functionalized to enhance solubility and reactivity. Commonly used functionalization methods include covalent functionalization and non-covalent functionalization. Covalent functionalization is based on the formation of a covalent linkage between functional entities and the carbon skeleton of nanotubes. It could also be divided into direct covalent sidewall functionalization and indirect covalent functionalization with carboxylic groups on the surface of CNTs. Direct covalent sidewall functionalization is associated with a change in hybridization from sp2 to sp3 and a simultaneous loss of conjugation (e.g., fluorination of nanotubes). Indirect covalent functionalization takes advantage of chemical transformations of carboxylic groups at the open ends and holes in the sidewalls. These carboxylic groups might have existed on the as-grown CNTs and also be further generated during oxidative purification. In order to increase the reactivity of CNTs, the carboxylic acid groups usually need to be converted into acid chloride and then undergo an esterification or amidation reaction.

Non-covalent functionalization is mainly based on supramolecular complexation using various adsorption bonding forces, such as Van der Waals force, hydrogen bonds, electrostatic force and π-stacking interactions. Compared to the chemical functionalization, non-covalent functionalization has the advantages that it could be operated under relatively mild reaction conditions to maintain the graphitic structure of CNTs.

In some embodiments, single-walled carbon nanotubes (SWCNTs), multi-walled carbon nanotubes (f-MWCNT), or any fibrillar (aspect ratio greater than 1) macromolecule are covalently functionalized with aliphatic primary amino groups or other ionizable molecular appendicies.

In some embodiments, the functionalized SWCNTs (fSWCNTs), functionalized multi-walled carbon nanotubes (f-MWCNT), or any fibrillar (aspect ratio greater than 1) macromolecule have an average length of about 30-3000 nm, 30-1000 nm, 30-300 nm, 30-100 nm, 100-3000 nm, 100-1000 nm, 100-300 nm, 300-3000 nm or 300-1000 nm. In some embodiments, the functionalized SWCNTs (fSWCNTs), functionalized multi-walled carbon nanotubes (f-MWCNT), or any fibrillar (aspect ratio greater than 1) macromolecule have an average length of about 100-600 nm, 100-500 nm, 100-400 nm, 200-600 nm, 200-500 nm, 200-400 nm or 250-350 nm. In some embodiments, the functionalized SWCNTs (fSWCNTs), functionalized multi-walled carbon nanotubes (f-MWCNT), or any fibrillar (aspect ratio greater than 1) macromolecule have an average length of about 300 nm.

In some embodiments, the functionalized SWCNTs (fSWCNTs), functionalized multi-walled carbon nanotubes (f-MWCNT), or any fibrillar (aspect ratio greater than 1) macromolecule have an average diameter of about 0.1-30 nm, 0.1-10 nm, 0.1-3 nm, 0.1-1 nm, 0.1-0.3 nm, 0.3-30 nm, 0.3-10 nm, 0.3-3 nm, 0.3-1 nm, 1-30 nm, 1-10 nm, 1-3 nm, 3-30 nm, 3-10 nm or 10-30 nm. In some embodiments, the functionalized SWCNTs (f-SWCNTs) have an average diameter of about 0.5-1.5 nm, 0.6-1.4 nm, 0.7-1.3 nm, 0.8-1.2 nm or 0.9-1.1 nm. In some embodiments, the functionalized SWCNTs (f-SWCNTs), functionalized multi-walled carbon nanotubes (f-MWCNT), or any fibrillar (aspect ratio greater than 1) macromolecule have an average diameter of about 1 nm. In other embodiments, the functionalized SWCNTs (f-SWCNTs) have an average diameter of about 1-1.8 nm, 1.2-1.6 nm or 1.3-1.5 nm. In some embodiments, the functionalized SWCNTs (f-SWCNTs), functionalized multi-walled carbon nanotubes (f-MWCNT), or any fibrillar (aspect ratio greater than 1) macromolecule have an average diameter of about 1.4 nm.

Therapeutic Agents

The therapeutic agents include any agent that prevents or reduces kidney or liver injury and is capable of attachment to f-CNTs. In some embodiments, the therapeutic agents include small molecule drugs, proteins, peptides, polynucleotides and mixtures thereof. In some embodiments, the therapeutic agents are RNAs, such as siRNAs, premature miRNAs, single-stranded mature miRNAs, double-stranded mature miRNAs or antisense mRNAs targeting one or more genes involved in kidney or liver injury. In some embodiments, the one or more genes involved in kidney or liver injury are selected from the group consisting of MMP-9, JNK, Epas1, Hif1an, Ac1, Fih1, Irp1, Egln1, Egln2, Egln3, PHD1, PHD2, PHD3, CTR1, CTR2, cFOS, FOS, cJUN, JUN, Fra1, Fra2, ATP, AP-1, MEP1A, MEP1B, VIM, p53, FASR, FASL, COL3A1, Kim-1 and C3 gene.

In some embodiments, therapeutic agents are therapeutic RNAs, such as siRNAs, premature miRNAs, single-stranded mature miRNAs and/or double-stranded mature miRNAs that inhibit expression of the one or more genes involved in kidney or liver injury as describe above. The therapeutic RNAs are non-covalently linked to f-CNTs, preferably f-SWCNTs, through electrostatic and hydrogen bonding to the carbon nanotubes via titration of nanotubes and RNA complexes together. In some embodiments, the therapeutic RNAs are mixed with nanotubes at a molar ratio ranging from 1:10, 1:5, 1:2, preferably 1:2 or 1:1, followed with sonication. Sonication may be performed in a variety of ways, including probe tip ultrasonication and the milder bath sonication.

The RNA-f-CNT complex will remain linked at a certain extracellular concentration (e.g., ≥50 nM). However, once the RNA-f-CNT complex enters the intercellular environment, the internalization and compartmentalization, plus the loss of undelivered construct through renal elimination, will dilute the concentration to levels where the therapeutic RNA will dissociate from the f-CNT (e.g. <1 nM).

In other embodiments, the therapeutic RNAs are conjugated to f-CNTs via a cleavable sulfide bond that will then be cleaved within the intercellular environment to release the therapeutic RNAs.

In some embodiments, f-CNT linked therapeutic RNAs are prophylactically delivered to the specific cell types in the kidney and/or liver where the f-CNTs localize, thereby reducing the damage caused to the organ. For example, liver sinusoidal endothelial cells (LESCs) form a barrier around hepatocytes and function as scavengers, protecting hepatocytes from toxins in the bloodstream. Damage to these cells can lead to vascular occlusive disorder, which can cause liver problems. Such damage to the liver may be prevented by prophylactic administration of therapeutic RNAs linked to the f-CNTs. In some embodiments, the therapeutic RNAs are designed to target genes whose knockdown may ameliorate the damage caused to the kidney. Examples of such genes include, but are not limited to: MMP-9, JNK, Epas1, Hif1an, Ac1, Fih1, Irp1, Egln1, Egln2, Egln3, PHD1, PHD2, PHD3, CTR1, CTR2, cFOS, FOS, cJUN, JUN, Fra1, Fra2, ATP, AP-1, MEP1A, MEP1B, VIM, p53, FASR, FASL, COL3A1, Kim-1 and C3 gene.

In some embodiments, the therapeutic RNAs are designed to target genes whose knockdown may ameliorate the damage to the proximal tubule cells (PTC) of the kidney, which often lead to acute kidney injury (AKI). Examples of such genes include, but are not limited to: MMP-9, JNK, Epas1, Hif1an, Ac1, Fih1, Irp1, Egln1, Egln2, Egln3, PHD1, PHD2, PHD3, CTR1, CTR2, cFOS, FOS, cJUN, JUN, Fra1, Fra2, ATP, AP-1, MEP1A, MEP1B, VIM, p53, FASR, FASL, COL3A1, Kim-1 and C3 gene.

In other embodiments, the therapeutic RNAs are designed to target genes whose knockdown may ameliorate the damage caused to the liver, Examples of such genes include, but are not limited to: MMP-9, JNK, Epas1, Hif1an, Ac1, Fih1, Irp1, Egln1, Egln2, Egln3, PHD1, PHD2, PHD3, CTR1, CTR2, cFOS, FOS, cJUN, JUN, Fra1, Fra2, ATP, AP-I, MEP1A, MEP1B, VIM, p53, FASR, FASL, COL3A1, Kim-1 and C3 gene.

In some embodiments, the therapeutic RNAs are siRNAs. In some embodiments, the siRNAs are siRNAs that inhibit expression of genes selected from the group consisting of MMP-9, JNK, Epas1, Hif1an, Ac1, Fih1, Irp1, Egln1, Egln2, Egln3, PHD1, PHD2, PHD3, CTR1, CTR2, cFOS, FOS, cJUN, JUN, Fra1, Fra2, ATP, AP-1, MEP1A, MEP1B, VIM, p53, FASR, FASL, COL3A1, Kim-1 and C3 gene. In some embodiments, the siRNAs are siRNAs that inhibit expression of the MMP-9, JNK, Epas1, Hif1an, Ac1, Fih1, Irp1, Egln1, Egln2, Egln3, PHD1, PHD2, PHD3, CTR1, CTR2, cFOS, FOS, cJUN, JUN, Fra1, Fra2, ATP, AP-1, MEP1A, MEP1B, VIM, p53, FASR, FASL, COL3A1, Kim-1 and C3 gene. In some embodiments, the siRNAs are selected from the groups consisting of MMP-9, JNK, Epas1, Hif1an, Ac1, Fih1, Irp1, Egln1, Egln2, Egln3, PHD1, PHD2, PHD3, CTR1, CTR2, cFOS, FOS, cJUN, JUN, Fra1, Fra2, ATP, AP-1, MEP1A, MEP1B, VIM, p53, FASR, FASL, COL3A1, Kim-1 and C3 gene.

In some embodiments, the therapeutic RNAs are precursor miRNAs. In some embodiments, the therapeutic RNAs are mature single-stranded miRNAs. In some embodiments, the therapeutic RNAs are mature double-stranded miRNAs. In some embodiments, the therapeutic RNAs are antisense RNAs.

In some embodiments, the f-CNT-therapeutic RNA conjugates of the present application have an average molecular weight of about 0.5-100 k, 5-10 k, 5-50 k, 5-100 k, 5-600 k, 100-500 k, 100-400 k, 100-300 k, 100-200 k, 200-600 k, 200-500 k, 200-400 k 200-300 k, 300-600 k, 300-500 k, 300-400 k, 400-600 k, 400-500 k or 500-600 k Dalton. In some embodiments, the f-CNT-therapeutic RNA conjugates of the present application have an average molecular weight of about 1-500 k, 1-400 k or 2.5-400 k Dalton. In some embodiments, the f-CNT-therapeutic RNA conjugates of the present application have an average molecular weight of about 300-350 k, about 300 k or about 350 k Dalton. In some embodiments, the f-CNT-therapeutic RNA conjugates exhibit rapid blood clearance (e.g., t1/2 of about 120, 100, 90, 75, 60, 45, 30, 15, 12, 10, 9, 8, 7, 6, 5, 4, 3, 2 or 1 min.); minimal liver and kidney and spleen accumulation; and a combination of renal and biliary elimination of 1-100/, 50-60%, 60-70%, 70-80%, 80-90%, or over 90% of the injected dose within one hour of intravenous administration.

Pharmaceutically Acceptable Carrier

As used herein, the phrase "pharmaceutically acceptable carrier" includes any and all molecular entities and compositions that are of sufficient purity and quality for use in the formulation of a composition or medicament of the present application and that, when appropriately administered to an animal or a human, do not produce an adverse, allergic or other untoward reaction. Since both human use (clinical and over-the-counter) and veterinary use are equally included within the scope of the present invention, a pharmaceutically acceptable formulation would include a composition or medicament for either human or veterinary use. In one embodiment, the pharmaceutically acceptable carrier is water or a water based solution. In another embodiment, the pharmaceutically acceptable carrier is a non-aqueous polar liquid such as dimethyl sulfoxide, polyethylene glycol and polar silicone liquids. In another embodiment, the carrier could be liposomal or polymeric agents. The use of such media and agents with pharmaceutically active substances is well known in the art. Except insofar as any conventional media or agent is incompatible with the f-CNT-therapeutic agent conjugates, its use in the therapeutic compositions is contemplated.

Formulation

The pharmaceutical composition of the present application may be formulated in a dosage form for the desired route of administration. The amount of the f-CNT-therapeutic agent conjugates which can be combined with the carrier material to produce a single dosage form will vary depending upon the host being treated, and the particular mode of administration. The amount of the f-CNT-therapeutic agent conjugates that can be combined with the carrier material to produce a single dosage form will generally be that amount of the conjugate which produces a therapeutic effect.

Formulations suitable for parenteral administration comprise the f-CNT-therapeutic agent conjugates in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The pharmaceutical compositions of the present application may also contain adjuvants such as preservatives, wetting agents, emulsifying agents and dispersing agents. Prevention of the action of microorganisms upon the subject compositions may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions.

Route of Administration

The pharmaceutical composition of the present application may be administered intravenously, intra-arterially or in other suitable ways to a subject in need of such treatment. Administration of the pharmaceutical composition can occur for a period of seconds, hours, days or weeks depending on the purpose of the pharmaceutical composition usage. In some embodiments, the pharmaceutical composition of the present application is administered intravenously.

In some embodiments, the pharmaceutical composition of the present application is administered by direct infusion into the kidney through the renal vein. In other embodiments, the pharmaceutical composition of the present application is administered by direct infusion into the liver through the hepatic vein.

In some embodiments, administration of the pharmaceutical composition of the present application is performed parenterally. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

Dose

The dosage level of the pharmaceutical composition of the present application will depend upon a variety of factors including the activity of the particular composition of the present invention employed, the route of administration, the time of administration, the rate of excretion or metabolism of the particular composition being employed, the duration of the treatment, other drugs, compounds and/or materials used in combination with the particular composition employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compositions of the invention employed in the pharmaceutical composition at levels lower than that required to achieve the desired therapeutic effect and then gradually increasing the dosage until the desired effect is achieved.

As a general proposition, the therapeutically effective amount of the agent-f-CNT conjugate of the present application are administered in the range of about 0.1 pg/kg body weight/day to about 100000 mg/kg body weight/day whether by one or more administrations. In some embodiments, the range of each active agent administered daily is from about 100 pg/kg body weight/day to about 50 mg/kg body weight/day, 100 pg/kg body weight/day to about 10 mg/kg body weight/day, 100 pg/kg body weight/day to about 1 mg/kg body weight/day, 100 pg/kg body weight/day to about 10 mg/kg body weight/day, 500 pg/kg body weight/day to about 100 mg/kg body weight/day, 500 pg/kg body weight/day to about 50 mg/kg body weight/day, 500 g/kg body weight/day to about 5 mg/kg body weight/day, 1 mg/kg body weight/day to about 100 mg/kg body weight/day, 1 mg/kg body weight/day to about 50 mg/kg body weight/day, 1 mg/kg body weight/day to about 10 mg/kg body weight/day, 5 mg/kg body weight/dose to about 100 mg/kg body weight/day, 5 mg/kg body weight/dose to about 50 mg/kg body weight/day, 10 mg/kg body weight/day to about 100 mg/kg body weight/day, and 10 mg/kg body weight/day to about 50 mg/kg body weight/day. In some embodiments, the agent-f-CNT conjugate of the present application is administrated daily at the above-described doses for 1, 2, 3, 4, 5, 6, 7, 8, 9, 10, 11, 12, 13 or 14 days. In some embodiments, the agent-f-CNT conjugate of the present application is administrated daily at the above-described doses for a period prescribed by the physician or veterinarian to chronically treat a medically necessary condition.

In some embodiments, a therapeutically effective dose of f-CNT/therapeutic RNA conjugate is in the range of 0.1-1000 mg f-CNT+0.01-100 mg therapeutic RNA per kg per day for 3-7 days. In some embodiments, the agent-f-CNT conjugate of the present application is administrated daily at the above-described doses for a period prescribed by the physician or veterinarian to chronically treat a medically necessary condition.

Composition

Another aspect of the present application relates to pharmaceutical compositions comprising the therapeutic agent-f-CNT conjugates of the invention and pharmaceutically acceptable excipients.

In another aspect of the present application, the present invention includes a composition comprising single-walled carbon nanotubes, multi walled carbon nanotubes, or other fibrillar molecule that have been non-covalently linked to therapeutic RNA molecules.

Disease Conditions

The compositions and methods of the present application may be used for the treatment of disease conditions such as anemia, liver sinusoidal injury, acute kidney injury or acute renal failure, liver injury, rhabdomyolysis, contrast-induced nephropathy, chronic kidney disease and any disease condition that may be treated by a reduction in BUN-to-creatinine ratio. In certain embodiments, the compositions and methods of the present application may be used for the treatment of any acute and/or chronic renal and/or hepatic injury or disease and any complications arising from those injuries.

A "subject" refers to either a human or non-human animal. Examples of non-human animals include vertebrates, e.g., mammals, such as non-human primates (particularly higher primates), dogs, rodents (e.g., mice, rats, or guinea pigs), pigs and cats, etc. In a preferred embodiment, the subject is a human.

In certain embodiments, methods and pharmaceutical compositions of the present application can be employed in combination therapies, that is, the methods and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive composition may be administered concurrently with another anti-proliferative agent), or they may achieve different effects (e.g., control of any adverse effects).

In some embodiments, the pharmaceutical composition of the present application is used before, after or concurrently, with a nephrotoxic or hepatoxic drug or a medical procedure to prevent or reduce renal injury or liver injury caused by the drug or medical procedure. Nephrotoxic and/or hepatotoxic drugs include, but are not limited to, antibiotics, such as aminoglycosides, sulfonamides, amphotericin B, foscarnet, quionlones (e.g., ciprofloxacin), rifampin, tetracycline, acyclovir, pentamidine, vanomycin; chemotherapeutics and immunosuppressants, such as cisplatin, methotrexate, mitomycin, cyclosporine, ifosphamide, zoledronic acid; antihyperlipidemics, such as statin drugs (rhabdomyolysis) or gemfibrozil; drugs of abuse, such as cocaine, heroin, methamphetamine, or methadone; and other miscellaneous drugs, such as chronic stimulant laxative use, radiographic contrast, ACE inhibitors, NSAIDs, aspirin, mesalamine (e.g., asacol, pentasa), and aristocholic acid. In some embodiments, the pharmaceutical composition of the present application is used before, after or concurrently, to a medical procedure to prevent ischemic injury or treat or prevent injury from sepsis.

In one embodiment of the invention, ammonium functionalized carbon nanotubes have been deployed to deliver bioactive siRNA to renal PTC as a pharmacological strategy to prevent nephrotoxic injury. A therapeutically effective dose of f-CNT/siRNA in mice was 1.6 mg f-CNT+0.087 mg siRNA per Kg per day for 3-5 days. These doses of f-CNT/siRNA were also sufficient to achieve a relative knock-down of Ctrl and EGFP and were well tolerated by the host. This regimen achieved prophylaxis with a cumulative dose of ~0.4 mg siRNA/Kg in comparison with other delivery platforms for gene silencing that required cumulative dosages that approached 7.5 mg/kg in mouse models (1 log less siRNA). The drug constructs and their components were found to be well tolerated and safe at the doses employed. The analysis of kidneys from animals in the f-CNT/siMep1b/siTrp53 group showed significantly lower levels of macrophage, leukocyte, and T cell infiltration within the kidney cortex at 14 and 180 days post cisplatin treatment compared to controls. Longer term fibrosis was also reduced in the combination drug group. These results show that fibrillar nanocarbon-mediated RNAi treatment successfully minimizes renal injury from a nephrotoxic cisplatin dose. Histopathology as assayed by H and E staining also confirmed statistically improved tissue morphology. Therefore, this is a pharmacological intervention that improves progression-free survival, reduces fibrosis and decreases immune cell infiltration in subjects.

Below are disclosed methods and systems for targeting the delivery of therapeutic agents to specific cell types in mammals, in particular the kidney and liver. Further aspects and advantages of the application will appear from the following description taken together with the accompanying drawings.

EXAMPLES

Example 1: Materials and Methods

Synthesis and Characterization of the Soluble, Functionalized Single Walled Carbon Nanotube Construct.

The f-CNT were prepared and characterized via covalent cycloaddition of azomethine ylides with SWCNT. McDevitt, et al., PloS One 2, e907 (2007); McDevitt, et al., Society of Nuclear Medicine 48, 1180-1189 (2007); Ruggiero, et al., Proceedings of the National Academy of Sciences of the United States of America 107, 12369-12374 (2010); Alidori, et al., The Journal of Physical Chemistry. C, Nanomaterials and Interfaces 117, 5982-5992 (2013); Villa, et al., Nano Letters 8, 4221-4228 (2008). Characterization using different analytical techniques (Transmission Electron Microscopy (TEM), Dynamic-Light-Scattering (DLS), Kaiser assay, RP-HPLC and spectrofluorometric titration with siRNA sequences) revealed an amine content of 0.3 mmol/g of f-CNT and chemical purity >99%. Dicer validated RNA sequences (Hefner, et al., Journal of Biomolecular Techniques: JBT 19, 231-237 (2008)) were designed to silence enhanced green fluorescent protein (EGFP), murine copper transport protein 1 (Ctrl), meprin-1β (Mep1b), and p53 (Trp53); a non-specific scrambled sequence (Scram) was used as a control. The non-covalent binding of f-CNT and siRNA was quantified and the binding affinities were ~5 nmol/L and up to 4 siRNA could be loaded per f-CNT under physiological conditions. Alidori, et al., The journal of physical chemistry. C, Nanomaterials and interfaces 117, 5982-5992 (2013). TEM of solid f-CNT and f-CNT/siEGFP (1:1 complex) was performed and showed a f-CNT average length of 300 nm; both samples were water soluble (10 g/L), could be resolved chromatographically, and were rapidly renally filtered in a murine model. Ruggiero, et al., Proceedings of the National Academy of Sciences of the United States of America 107, 12369-12374 (2010); Mulvey, et al., Nature nanotechnology 8, 763-771 (2013). DLS analyses provided evidence in aqueous solution that the molecular lengths of f-CNT and f-CNT/siEGFP (1:1) were comparable (intensity-based mean diameters were 356.2±14.2 nm and 332.7+10.6 nm, respectively) and indicated that the assembled drug construct was not an aggregate of cross-linked molecules.

High pressure carbon monoxide (HiPCO) produced single walled carbon nanotubes (SWCNT, >90% purity) were purchased from NanoLab, Inc. (Menlo Park, Calif.). Pristine SWCNT were mildly oxidized in 3M nitric acid (Fisher Scientific, Waltham, Mass.) to remove metallic impurities. These acid-treated SWCNT were then reacted with the Boc-amine precursor, 2-(2-(2-(2-(tert-butoxycarbonyl)aminoethoxy)ethoxy)ethylamino) acetic acid (Discovery ChemScience LLC, Princeton, N.J.) to yield SWCNT-NHBoc. Georgakilas, et al., Chem Commun, 3050-3051 (2002); Alidori, et al., The journal of physical chemistry. C, Nanomaterials and interfaces 117, 5982-5992 (2013). The SWCNT-$NH_2$ product (f-CNT) was purified by reverse phase chromatography after deprotecting the Boc-amine. Briefly, the crude f-CNT was dissolved in 0.1 M tetraethylammonium acetate ((TEAA), Fisher) and adjusted to pH 7. Acetonitrile (Fisher) was added to a final v/v of 20%. A Seppak Plus C18 cartridge (Waters) was equilibrated with 20% acetonitrile/0.1 M TEAA. The SWCNT-$NH_2$ was loaded onto the cartridge and washed extensively with 20% acetonitrile/0.1 M TEAA at 1 mL/min. The purified SWCNT-$NH_2$ was eluted from the cartridge in 50% acetonitrile/water and the solvent evaporated to yield the purified SWCNT-$NH_2$ solid. Purity and identity of the f-CNT were assessed by UV-Vis spectroscopy, HPLC, transmission electron microscopy (TEM) and dynamic light scattering (DLS). Alidori, et al., The journal of physical chemistry. C, Nanomaterials and interfaces 117, 5982-5992 (2013). Analytical HPLC was performed on a Beckman Coulter System Gold chromatography system equipped with in-line UV/Vis spectrum detector and tunable multi-wavelength fluorescence detector (Jasco FP-2020). Radioactivity was monitored through the use of an inline γ-RAM Model 3 radioactivity detector (IN/US). The stationary phase was a Gemini (Phenomenex, Torrence, Calif.) C18 column (5ip, 250×4.6 mm) column. A 0-to-100% mobile phase gradient of 0.1M TEAA, pH 6.5 and acetonitrile was used at a flow rate of 1.0 mL/min for 30 minutes. TEM analysis was performed using 200 mesh grids coated with carbon support film and viewed on a JEOL JEM 1400 TEM with a LaB6 filament. Images were taken using an Olympus SIS Veleta 2kx2k side mount camera. DLS was performed using a Zetasizer Nano ZS system equipped with a narrow bandwidth filter (Malvern Instruments, MA).

All buffers were prepared with RNAse-free water rendered metal-free by Chelex 100 resin pre-treatment. Briefly, 0.050 mL of 0.7 mM sense EGFP-$NH_2$ was buffered to pH 9.5 with 0.100 mL of a 0.1 M sodium bicarbonate solution. The buffered sense EGFP-$NH_2$ solution was then reacted with 0.100 mL of 10 mg/mL aqueous solution of 2-(4-isothiocyanatobenzyl)-1,4,7,10-tetraazacyclododecane-1,4,7,10-tetraacetic acid (p-SCN-Bz-DOTA, Macrocyclics). The reaction mixture was stirred at ambient temperature for 1 h and then purified by size exclusion with a 10-DG column (BioRad, Hercules, Calif.) eluted using metal-free water to yield the sense EGFP-DOTA product. HPLC, UV-Vis and MALDI-TOF mass spectrometry was used to characterize the product. Radiolabeling was performed by buffering 0.200 mL of a 0.041 mM sense EGFP-DOTA to pH 5 with 0.090 mL of 1 M ammonium acetate ($NH_4Ac$, Fisher) and the subsequent addition of 14 MBq of indium chloride ($^{111}InCl_3$, Perkin Elmer). The labeling reaction mixture was heated at 60° C. for 30 minutes and then quenched with 0.200 mL of 0.01 M ethylenediaminetetraacetic acid (EDTA, Fisher). The labeled EGFP was purified by size exclusion with a 10-DG column eluted with PBS. The sense EGFP-[$^{111}$In]DOTA strand was then annealed with the complementary anti-sense strand in annealing buffer (10 mM Tris, 50 mM NaCl, 1 mM EDTA, pH 7.5) with heating to 95° C. for 4 minutes. The radiochemical purity of the product was assayed using reverse-phase radio-HPLC and radioactivity was monitored through an inline γ-RAM Model 3 radioactivity detector.

The SWCNT-[($^{86}$Y]DOTA)(AF488)(AF680)] construct was prepared by adding 300 MBq (8.1 mCi) of acidic 86Y chloride (Memorial Sloan-Kettering Cancer Center Cyclotron Core) to 0.400 mg of a 1 g/L solution of f-CNT in metal-free water (MFW) and 0.050 mL of 3M ammonium acetate (Aldrich) and 0.015 mL of 150 g/L 1-ascorbic acid (Aldrich) to yield a pH 5.0 solution. The solution was clear and dark green-brown in color. The reaction was heated at 61° C. for 45 min., quenched with 0.040 mL of 50 mM diethylenetriaminepentaacetic acid (DTPA, Aldrich), and then purified by size exclusion chromatography using a P6 resin (BioRad) as the stationary phase and 1% human serum albumin (HSA, Swiss Red Cross) in 0.9% NaCl (Abbott Laboratories) as the mobile phase. An aliquot of the final product, [$^{86}$Y]f-CNT, was used to determine the radiochemical purity by instant thin layer chromatography using silica gel. Further spectroscopic, radiometric, and chromatographic characterization of the construct was performed by reverse phase HPLC. In-111 was obtained from MDS Nordion (Vancouver) for other tracer experiments. The SWCNT-[(DOTA)(AF488)(AF680)] and SWCNT-[DOTA] construct was labeled using materials and methods similar to those described above for the $^{86}$Y radiochemical labeling process. Both radionuclides have demonstrated similar labeling kinetics, purities, and yields in reactions with SWCNT-[(DOTA)(AF488)(AF680)] and SWCNT-[(DOTA)].

siRNA Sequences

Dicer validated RNA sequences (Hefner, et al., Journal of biomolecular techniques: JBT 19, 231-237 (2008)) were designed to silence enhanced green fluorescent protein (EGFP), mouse copper transport protein 1 (Ctr1), mouse meprin-1β (Mep1b), mouse p53 (Trp53) and were obtained from Integrated DNA Technologies, Inc. (IDT, Coralville, Iowa) along with a non-specific scrambled sequence (Scram). The following (sense (s) and antisense (as)) sequences were used:

```
siEGFP:
                                           (SEQ ID. NO: 1)
5'GCAAGCUGACCCUGAAGUUCAUtt3', (s)

(SEQ ID. NO: 2)
5'AUGAACUUCAGGGUCAGCUUGCCG3' (as),
and (SEQ ID. NO: 3)
5'NH2-(CH2)6-GCAAGCUGACCCUGAAGUUCAUtt3' (amine-
modified sense);
and (SEQ ID. NO: 4)
5'Cy3(CH2)2C(O)NH-(CH2)6-GCAAGCUGACCCUGAAGUUCAUtt3'
(Cyanine 3 succinimidyl ester modified sense;
TriLink Inc., San Diego, CA);

siScram:
                                           (SEQ ID. NO: 5)
5'CGUUAAUCGCGUAUAAUACGCGUAt3' (s)
and (SEQ ID. NO: 6)
5'CAGCAAUUAGCGCAUAUUAUGCGCAUA3' (as);

siCtr1:
                                           (SEQ ID. NO: 7)
5'GGCAUGAACAUGUGAAUUGCUGGTT3' (s)
and (SEQ ID. NO: 8)
3'GUCCGUACUUGUACACUUAACGACCAA5' (as);

siMep1b:
                                           (SEQ ID. NO: 9)
5'GGAAUUGACCAAGACAUAUUU GATA3' (s)
and (SEQ ID. NO: 10)
3'CUCCUUAACUGGUUCUGUAUAAACUAU5' (as);
and siTrp53:
                                           (SEQ ID. NO: 11)
5'AGGAGUCAC AGUCGGAUAUCAGCCT3' (s)
and (SEQ ID. NO: 12)
3'CCUCCUCAGUGUCAGCCUAUAGUCGGA5' (as).
```

Cell Culture Experiments

HeLa cells expressing EGFP (EGFP$^+$HeLa, Cell Biolabs, San Diego, Calif.) were cultured at 37° C. and 5% $CO_2$ in high glucose DMEM (Life Technologies, Grand Island, N.Y.) supplemented with 10% FBS (Life Technologies), 0.1 mM MEM non-essential amino acid solution (NEAA, Life Technologies), 2 mM L-Glutamine (Life Technologies), and 0.010 mg/mL Blasticidin (Life Technologies).

The kinetics of internalization of f-CNT/siEGFP was evaluated and quantified in EGFP$^+$HeLa cells using two different methods:

(1) Confocal microscopy was used to image internalization in real time and employed the fluorescent siEGFP-Cy3 sequence. The f-CNT/siEGFP-Cy3 construct was prepared by annealing equimolar amounts of f-CNT and siRNA and adjusted to a final concentration of 50 nM in Opti-MEM (Life Technologies) in the plate wells. The siEGFP-Cy3 alone was used as control at the same concentration. Cells were seeded at a density of $2.5 \times 10^4$ cells per well in a 24-well plate, using serum-free DMEM and incubated overnight at 37° C. and 5% $CO_2$. The cells (n=3 wells per group) were then suffused with 50 nM Opti-MEM solutions of f-CNT/siEGFP-Cy3 or siEGFP-Cy3 alone. The internalization of the Cy3-labeled oligonucleotide was imaged every 0.50 h for 5 h by confocal microscopy using a LSM 5 microscope (Zeiss) (FITC laser excitation: 488 nm; TRITC laser excitation: 561 nm; DIC channel). Images were elaborated with Metamorph 7.8.1.0 (Molecular Devices, Sunnyvale, Calif.).

(2) Radionuclide-based internalization of siEGFP-[$^{111}$In]DOTA was quantified using a cell-stripping assay performed under similar conditions. Cells were seeded at 80% confluence in 6-well plates and incubated overnight as described above. The cells (n=3 wells per group per time-point) were then suffused with 50 nM Opti-MEM solutions containing 118.4 MBq of f-CNT/siEGFP-[$^{111}$In]DOTA or siEGFP-[$^{111}$In]DOTA alone (specific activity of 59.2 MBq/g). The supernatant was removed at each time-point (30, 60, 90, 120, 180, 240 and 300 min.) and the cells washed 3 times with 2 mL of ice-cold PBS. The residual radioactivity on the outer cell membrane was stripped-off at pH 2.8 with a 50 mM glycine/150 mM NaCl solution for 10 minutes at 4° C. Cells were again washed with ice-cold PBS and detached from the plate with Trypsine-EDTA (0.25%) (Mediatech, Inc., Manassas, Va.); counted on a hemocytometer; pelleted; and the radioactivity counted on a γ-counter (Packard Cobra, GMI, Inc., Ramsey, Minn.) using the 15-550 keV window. Aliquots of the 50 nM Opti-MEM solutions that contained f-CNT/siEGFP-[$^{111}$In]DOTA or siEGFP-[$^{111}$In]DOTA were counted and used to quantify the amount of siRNA that accumulated per cell.

EGFP$^+$HeLa cells were used to investigate f-CNT/siEGFP silencing in vitro using flow cytometry, confocal microscopy, Western blot analyses, and quantitative RT-PCR. Cells were seeded in 24-well plates at a density of $2.5 \times 10^4$ cells per well using serum-free DMEM and incubated overnight. Lipofectamine 2000 (Lf, Life Technologies) transfection was included as a positive control to confirm that the siRNA was bioactive.

Flow cytometry was used to investigate the change in green fluorescence intensity in cells that were cultured in a 50 nM solution of (a) f-CNT/siEGFP, (b) siEGFP alone, (c) Lf/siEGFP, (d) f-CNT/siScram, (e) f-CNT alone, or (f) PBS vehicle in triplicate at 37° C. and 5% $CO_2$. Cells were harvested and analyzed with a BD Acuri C6 cytometer (BD Biosciences, San Jose Calif.) to measure EGFP fluorescence intensity at 1, 2, and 3 days. Data were analyzed using FlowJoX10 software (FlowJo, LLC, Ashland, Oreg.).

Microscopy was used to image the change in green cell fluorescence in real time. Cells were cultured in a 50 nM solution of (a) f-CNT/siEGFP, (b) siEGFP alone, or (c) Lf/siEGFP incubated at 37° C. and 5% $CO_2$ and imaged with a LSM 5 live microscope (Zeiss). Images of cells from 3 regions per well were collected every 30 minutes for 60 h post-transfection. EGFP$^+$HeLa cells were imaged using the FITC channel (Ex BP 450-490 nm, Em LP 515 nm) and the DIC channel. The images were analyzed using Metamorph 7.8.1.0 (Molecular Devices).

Western blot analysis was used to measure EGFP protein expression in EGFP$^+$HeLa cells that were incubated with 50 nM solution of (a) f-CNT/siEGFP, (b) siEGFP alone, (c) Lf/siEGFP, (d) f-CNT/siScram, (e) f-CNT alone, or (f) PBS vehicle in triplicate at 37° C. and 5% CO2. Cells were lysed with RIPA buffer (25 mM Tris-HCl pH 7.6, 150 mM NaCl, 1% NP-40, 1% sodium deoxychlolate, 0.1% SDS) on ice for 1 hour. Lysates were centrifuged at 13,000×g for 20 minutes. Supernatants were collected and measured for total protein concentration using DC Protein Assay (BioRad) according to the manufacturer's instructions. Equal amounts of protein (0.0075 mg) were heated at 95° C. for 5 minutes in 1× Laemlli sample buffer containing 2-mercaptoethanol. SDS-PAGE was carried out at 120V for 1 hour using 12% acrylamide gels. Electrophoretically separated proteins were transferred to a nitrocellulose membrane at 100V for 1 hour. Membrane was blocked in 5% non-fat milk in TBST buffer overnight at 4° C. On the following day, the nitrocellulose membranes were incubated with mouse anti-EGFP antibodies (Roche) at 1:10,000 dilution for 1 h at ambient temperature followed by horseradish peroxidase conjugated goat anti-mouse secondary antibodies at 1:20,000 dilution for 1 hour at ambient temperature. Protein bands were detected on X-ray film using an enhanced chemiluminescence system (ChemiDoc MP imaging system, BioRad). Glyceraldehyde 3-phosphate dehydrogenase (GAPDH) or β-actin was included as loading controls and were measured to evaluate protein loading using an anti-GAPDH pAb (R&D Systems) or anti-3-actin antibody.

Quantitative RT-PCR analysis was used to measure EGFP mRNA expression in EGFP$^+$HeLa cells that were incubated with 50 nM solution of (a) f-CNT/siEGFP, (b) siEGFP alone, (c) Lf/siEGFP, (d) f-CNT/siScram, (e) f-CNT alone, or (f) PBS vehicle in triplicate at 37° C. and 5% CO2. RNA extraction was carried out using RNeasy Plus Mini Kit (Qiagen) according the manufacturer's instructions. RNA quality and concentration was measured at 260 nm using a NanoDrop ND-1000 spectrophotometer (Thermo Fisher Scientific). Total RNA (150 ng) was reverse transcribed to cDNA using a First Strand cDNA Synthesis kit (Thermo Scientific) according to manufacturer's instructions. PCR reaction was carried out by adding 0.002 mL of cDNA (15 ng) to 0.010 mL of TaqMan RT-PCR Mastermix (Applied Biosystems), 0.001 mL of primers specific to EGFP (IDT), and 0.007 mL of UltraPure DNase/RNase-Free distilled water (Life Technologies). Data were normalized to GAPDH and are expressed as fold-change relative to no treatment controls.

EGFP$^+$HeLa cells were plated at 20% confluence in a 24-well plate and incubated for 24 h. Cells were seeded with 0.60 mL of f-CNT in high glucose DME media at different concentrations (10 to 200 mg/L) in triplicate. Controls included triplicates of untreated cells, and triplicates of cells seeded with 0.001 mL of Lf mixed with 0.05 mL of Opti-MEM and 0.55 mL of high glucose DME media. All cell groups were incubated at 37° C. for 24 h, washed, trypsinized with 0.20 mL of a mixture of 0.25% Trypsin and 1 mM EDTA for 5 minutes at 37° C. and quenched with 0.50 mL of high glucose DME media. Viability was evaluated by flow cytometry with a BD Acuri C6 cytometer (BD Biosciences) using propidium iodide (Life Technologies) to detect dead cells.

Immunohistochemical and Immunofluorescence Staining

Mice (♂, NCr/nu/nu, Taconic) received an IV injection of SWCNT-[([$^{111}$In]DOTA)(AF488)(AF680)] and SWCNT-[([$^{111}$In]DOTA)] containing 0.04 mg of SWCNT construct and 74 kBq (0.002 mCi) of $^{111}$In per mouse via the retroorbital sinus. The animals were placed into 4 groups of 3-5 mice per group. Each group was sacrificed with CO2 aspiration at 1 h, 3 h, 24 h and 7 d. Tissue samples (blood, heart, kidneys, muscle, bone, lung, stomach, spleen, liver, bile, small intestine (consisting of the duodenum, jejunum, and ileum), contents of the small intestine, large intestine (consisting of the cecum and colon), contents of the large intestine), and feces were harvested, weighed, and counted using a 7-counter (Packard Instrument Co.) with a 315 to 435 keV energy window. Standards of the injected formulation were counted to determine the % ID/g.

Mice (male, NCr/nu/nu, Taconic) received 0.01 mg of f-CNT-(AF488)(AF680)(DOTA) in 0.10 mL of 1% human serum albumin ((HSA, Swiss Red Cross, Bern, Switzerland) in 0.9% NaCl (Abbott Laboratories, North Chicago, Ill.)) administered intravenously (IV) via the retroorbital sinus. f-CNT was covalently modified with AlexaFluor 488 tetrafluorophenyl ester (AF488-TFP, Invitrogen), AF680-SE, and 2-(4-isothiocyanatobenzyl)-1,4,7,10-tetraazacyclododecane-1,4,7,10-tetraacetic acid (DOTA, Macrocyclics). Ruggiero, et al., Proceedings of the National Academy of Sciences of the United States of America 107, 12369-12374 (2010). The f-CNT-(AF488)(AF680)(DOTA) was assayed to contain 0.02, 0.04 and 0.4 mmol of AF488, AF680 and DOTA per gram of f-CNT, respectively. Representative constructs (L-300 nm; MW-300 kD) displayed 7-10 AF488, 14-20 AF680, and 140-200 DOTA moieties per f-CNT. Mice were euthanized at 1, 3, 5, 20, 40, 60, 180 min., 24 h and the liver, spleen and kidneys harvested for immunofluorescence (IF) analyses. Controls included tissue from mice that received no construct; mice the received only the hydrolyzed-AF488 dye; and isotype-control staining of tissues with a non-specific primary antibody. Harvested tissue was fixed overnight in 4% paraformaldehyde at 4° C., embedded in paraffin, and sectioned to obtain 0.005 mm thick samples. Widefield microscopy was performed with an Axioplan2 imaging microscope, equipped with AxioCam MRm Camera (Zeiss, Inc), using filter cubes for DAPI, AF488 and TRITC. Slides were also scanned with the FLASH scanner (Perkin Elmer) to get an overview of the tissue. Confocal microscopy was performed using an Inverted Leica TCS SP5 microscope (Leica Microsystems, Inc). All 3D rendering was done with Imaris (Bitplane).

The immunofluorescent staining was performed in the Molecular Cytology Core Facility of Memorial Sloan Kettering Cancer Center using Discovery XT processor (Ventana Medical Systems). The tissue sections were deparaffinized with EZPrep buffer (Ventana Medical Systems), antigen retrieval was performed with CC 1 buffer (Ventana Medical Systems) and sections were blocked for 30 minutes with Background Buster solution (Innovex) for anti-Alexa488, beta-catenin, Ibal, CSF-1R, GM130 and GFAP antibodies or with 10% normal rabbit serum (Vector Labs) in PBS for anti-CD31, Lyvel and LAMP2 antibodies. Anti-AF488 (Molecular Probes, cat. no. A-11094, 5 µg/mL), anti-β-catenin (Sigma Aldrich, cat. no. C2206, 5 pg/mL), anti-Ibal (Wako, cat. no. 019-19741, 0.5 pg/mL), anti-CSF-1R (Santa Cruz, cat. no. sc-692, 0.5 µg/mL) and anti-GFAP (DAKO, cat. no. Z0334, 1 µg/mL) antibodies were applied and sections were incubated for 5 hours, followed by 60 min. incubation with biotinylated goat anti-rabbit IgG (Vector labs, cat. no. PK6101) at 1:200 dilution. Anti-CD31 (DIANOVA, cat. no. DIA-310, 1 µg/mL) and anti-LAMP2 (Abcam, cat. no. ab13524, 0.5 pg/mL) antibodies were applied and sections were incubated for 5 hours, followed by 60 min. incubation with biotinylated rabbit anti-rat IgG (Vector labs, cat. no. PK-4004) at 1:200 dilution. Anti-Lyvel (R&D Systems, cat. no. AF2125, 1 µg/mL) antibodies were applied and sections were incubated for 3 h, followed by 60 min. incubation with biotinylated rabbit anti-goat IgG (Vector, cat #BA-5000) at 1:200 dilution. Anti-GM130 (BD Pharmingen, cat. no. 610823, 1 µg/mL) antibodies were applied and sections were incubated for 3 h., followed by 60 min. incubation with biotinylated horse anti-mouse IgG (Vector Labs, cat. no. MKB-22258) at 1:200 dilution. The detection was performed with Streptavidin-HRP D (DAB-Map kit, Ventana), followed by incubation with one of the following Tyramide Alexa Fluors (Invitrogen): AF488 (cat. no. T20922) only for anti-AF488, anti-AF546 (cat. no. T20933), anti-AF568 (cat. no. T20914), anti-AF594 (cat. no. T20935) or anti-AF647 (cat. no. T20936) prepared according to the manufacturer instructions with predetermined dilutions. Slides were counterstained with DAPI (Sigma Aldrich, cat. no. D9542, 5 µg/mL) for 10 min. and coverslipped with Mowiol.

Kidney, spleen and liver tissue sections were stained using a Discovery XT processor (Ventana Medical Systems) in the MSKCC Molecular Cytology Core Facility. Mice were euthanized according to approved protocols and tissues harvested and washed in ice-cold PBS, fixed for 24 h in 4% paraformaldehyde, embedded in OCT, frozen at −80° C., and cryo-sectioned to obtain 0.005 mm thick samples for fixed-frozen sections. The paraffin embedding process involved tissue fixation for 24 h in 4% paraformaldehyde, washed and stored at 4° C. in 70% ethanol and embedded in paraffin. The tissue sections were blocked for 30 min. in 10% normal goat serum and 2% bovine serum albumin (BSA) in PBS. After staining with the primary antibody, slides were incubated for 1 h with biotinylated goat anti-rabbit IgG (Vector labs, cat #: PK6101) with a 1:200 dilution. Secondary Antibody Blocker, Blocker D, Streptavidin-HRP and DAB detection kit (Ventana) were used according to the manufacturer's instructions for IHC. In the case of IF, detection was performed with streptavidin-HRP (Ventana) followed by incubation with green-fluorescent AlexaFluor 488 tyramide (Invitrogen, cat # T20922). Collagen type I and III staining was performed using the picrosirius red kit (Polysciences, Inc., Cat #24901) according to the manufacturer's instruction.

Animal Experiments

The experiments used female Balb/c mice (Taconic, Hudson, N.Y.) aged 6-7 weeks or 49-52 weeks; male nu/nu aged 8-12 weeks (Taconic); female C57BL/6 p53 null and female C57BL/6 wild-type (Jackson Labs, Bar Harbor, Me.) 6-8 week old. The β-actin-EGFP transgenic C57BL/6 mice were kindly provided from the Joyce laboratory at MSKCC (female, 8-10 week old).

Imaging was performed with the microPET Focus™ 120 (CTI Molecular Imaging) in a naïve mouse model. Mice (♂, NCr/nu/nu, Taconic) were maintained under 2% isoflurane/oxygen anesthesia during the scanning. One-hour list-mode acquisitions were commenced at the time of intravenous (IV) injection of 0.01 mg per mouse (initially 2.78 MBq (0.075 mCi)) of SWCNT-[([86Y]DOTA)(AF488)(AF680)] via a 27G tail vein catheter (Vevo MicroMarker TVA, Visual Sonics) placed in the lateral tail vein. For all in vivo experiments, housing and care were in accordance with the Animal Welfare Act and the Guide for the Care and Use of Laboratory Animals. The animal protocols were approved by the Institutional Animal Care and Use Committee at MSKCC. An energy window of 350-700 keV and a coincidence timing window of 6 ns were used. The resulting list-mode data were sorted into twelve 12-s (0-5 min), twelve 30-s (5-10 min) and fifty 60-s (10-60 min) time bins and into 2-dimensional histograms by Fourier rebinning, and transverse images were reconstructed in a 128×128×96 matrix by filtered back-projection. The image data were corrected for nonuniformity of the scanner response, dead time count losses, and physical decay to the time of injection. No correction was applied for attenuation, scatter, or partial-volume averaging. The measured reconstructed spatial resolution of the Focus 120 scanner is 1.6 mm full width at half maximum at the center of the field of view. The counting rates in the reconstructed images were converted to activity concentrations (percentage injected dose per gram of tissue (% ID/g)) by use of an empirically determined system calibration factor (MBq/mL/cps/voxel) derived from the imaging of a mouse-size phantom containing 18F.

Biodistribution studies of f-CNT/siEGFP-[$^{111}$In]DOTA versus siEGFP-[$^{111}$In]DOTA alone were conducted on 6-7 week old female Balb/c mice. The 1:1 (mol:mol) complex of f-CNT/siEGFP was assembled using the radiolabeled siEGFP-[$^{111}$In]DOTA component as the tracer. Briefly, the carrier siEGFP molecule (0.042 mL of a 0.020 mM solution) was mixed with the tracer siEGFP-[$^{111}$In]DOTA (0.094 mL containing 444 kBq of $^{111}$In activity) and this mixture was heated to 95° C. for 4 min. The annealed radiolabeled siEGFP was added to a solution of f-CNT (0.558 mL of a 1.47 mM solution) at ambient temperature in PBS. The siEGFP-only control was similarly annealed and used 0.042 mL of a 0.020 mM siEGFP solution mixed with siEGFP-[$^{111}$In]DOTA (0.094 mL containing 444 kBq) and this mixture was added to 0.558 mL of PBS at ambient temperature. A dose of 0.032 mg of f-CNT/siEGFP-[$^{111}$In]DOTA in 0.100 mL of 1% HSA was administered IV to each mouse in the experimental group (n=5); each animal in the control group (n=5) mice was injected with 0.002 mg of siEGFP-[$^{111}$In]DOTA in a 0.100 mL volume of HSA. Following injection, the mice were maintained under isofluorane-induced anesthesia for 1 h and then euthanized. Tissues (heart, kidneys, lung, spleen, liver, stomach, intestine, muscle and bone), blood, and urine were harvested, weighed, and counted using a γ-counter (Packard) with a 315 to 435 keV energy window. Standards of the injected formulation were counted to determine the percent of the injected dose (% ID) and % ID per gram (% ID/g) per tissue. Samples of the injected formulations and urine samples from each group were analyzed by HPLC.

The kidney accumulation of f-CNT/siEGFP-[$^{111}$In]DOTA was investigated as a function of dose and schedule. The following dose regimens of f-CNT/siEGFP-[$^{111}$In]DOTA in 1% HSA were administered per mouse per group (n=3): (i) 1×0.015 mg; (ii) 1×0.03 mg; (iii) 2×0.03 mg (spaced 1 h apart); (iv) 3×0.03 mg (spaced 1 h apart); and (v) 1 ×0.09 mg. Following injection, the mice were maintained under isofluorane-induced anesthesia for 1 h and then euthanized. Kidneys and blood were harvested, weighed, and counted using a γ-counter.

A characteristic daily dose to achieve RNAi was 0.032 mg of f-CNT/siRNA per 20 g mouse (comprised of 0.030 mg of f-CNT and 0.0017 mg siRNA). The lower limit of concentration necessary to assure that the f-CNT and siRNA remained bound in vivo was 0.015 mg per mouse or a half-dose. The renal and blood accumulation of activity following the administration of 0.5; 1; 2 (2×0.03 mg, spaced 1 h apart); 3 (3×0.03 mg, spaced 1 h apart); and 1 dose of 0.09 mg per mouse was studied. It was observed that the renal accumulation appeared to increase linearly with dose and further that the brush border reset after 1 hour. Ruggiero, et al., Proceedings of the National Academy of Sciences of the United States of America 107, 12369-12374 (2010). The brush border was saturated with the single 0.09 mg dose per mouse. Therefore, a maximum single dose should be approximately 0.06 mg. The other option could be multiple doses spaced 1 hour apart. This shows that the brush border accumulated activity was rapidly internalized, and the brush border resets within 1 h and is prepared to receive more drug. While the daily 0.03 mg dose per mouse was sufficient to achieve knock-down, there appears to be therapeutic window to increase the dosage as necessary. The absence of radioactive counts in the blood indicated that the biodistribution process was completed.

The EGFP knock-down in vivo experiment was conducted on β-actin-EGFP transgenic C57BL/6 mice arranged in 4 groups of mice (n=4 per group). The f-CNT/siEGFP drug for the Group I animals was prepared by mixing 0.064 mL of a 0.020 mM solution of siEGFP with a 0.576 mL of a 0.00112 mM f-CNT solution and 0.0704 mL of 10×PBS. The f-CNT/siScram control drug for the Group II animals was prepared in a similar fashion. The Group III mice received siEGFP alone that was prepared by mixing 0.064 mL of siEGFP with 0.646 mL of PBS. Group IV mice received only the PBS vehicle control. Each animal per group received a 0.220 mL IV daily injection of the respective drug/control for 3 consecutive days. Mice were sacrificed 1 day after the last injection. Tissues were harvested and fixed frozen for histological studies. Images were acquired with an inverted fluorescence microscope (Nikon Ti-Eclipse run with NIS-Elements Ar) and processed with FIJI. Schindelin, et al., Nature methods 9, 676-682 (2012). Region-of-interest (ROI) analysis was done on 20× magnification 0.010 mm thick sections imaged with WL (DIC like) DAPI and EGFP channel. Approximately 50 tubules per experimental or control image were quantified (over 300 cells per group). The FIJI Cell Counter plug-in (ImageJ 1.47k) was used. The Cell Counter plug-in was developed by Kurt DeVos, University of Sheffield, Academic Neurology.

The Ctrl knock-down and copper-64 uptake into kidneys in vivo study was conducted on 3 groups of 5 balb/c mice (female, 6-7 weeks old). The Group I mice received f-CNT/siCtrl that was prepared by mixing 0.042 mL of a 0.020 mM solution of siCtrl with 0.164 mL of f-CNT (0.0039 mM) and 0.396 mL of PBS. Group II control mice received a regimen of only the siCtrl that was prepared my mixing 0.042 mL of siCtrl and 0.458 mL of PBS. The Group III mice received only a regimen of the PBS vehicle. The dose regimens were the following: 0.033 mg of f-CNT/siCtrl, 0.002 mg of siCtrl, or the PBS vehicle administered in 0.100 mL PBS to each mouse per group every day for 3 consecutive days. On the third day, every animal received an IV injection of 133 kBq of $^{64}$CuCl$_2$ (Washington University) in NSS and were then sacrificed after 1 h. The kidneys, liver, heart, and blood were harvested, weighed, and radioactivity measured on a γ-counter. The % ID/g was evaluated by comparison with known standards.

Progression-free survival was evaluated in mice prophylactically treated to silence the renal expression of Ctrl protein in anticipation of a scheduled nephrotoxic dose of cisplatin. The two groups of female balb/c mice (10-12 month old) were (a) f-CNT/siCtrl (n=7) and (b) PBS vehicle (n=3). Each animal received a daily dose of 1.6 mg f-CNT+ 0.087 mg siCtrl per kg (1:1, mol/mol) or PBS vehicle in a volume of 0.100 mL by IV injection for 5 consecutive days. On day 3, a single IP dose of cisplatin (Sigma, 10 mg/Kg in NSS) was administered. Blood samples from each mouse were collected on days 0, 1 and 6 (from cisplatin administration); weights were recorded daily; and observations of activity were noted. Progression-free survival was analyzed using the Kaplan-Meier method to score outcomes of weight loss (>20% of initial mass), renal biomarker values (>3 standard deviations relative to untreated group mean), severe lethargy or death.

The effective and biocompatible f-CNT-mediated knockdown of p53 and Meprin-1β in vivo study employed 5 groups of female balb/c mice (2-3 months old) that were arranged as follows: (a) f-CNT/siMep1b (n=7); (b) f-CNT/siTrp53 (n=7); (c) siMep1b (n=7); (d) siTrp53 (n=7); and (e) PBS vehicle (n=3). Each animal received a daily 0.100 mL IV injection of 0.032 mg of the 1:1 (mol/mol) f-CNT/siRNA constructs, 0.002 mg of the siRNA alone, or the PBS vehicle for 3 consecutive days. Renal health was assessed on day 4 using a metabolic panel that assayed blood urea nitrogen (BUN), serum creatinine (sCr), phosphorous (P), and magnesium (Mg) as biomarkers of kidney injury; these assays were performed by the MSKCC Pathology Core laboratory. Kidneys were harvested on day 4, fixed, sectioned and stained with hematoxylin and eosin (H&E) to examine tissue morphology as a function of treatment. Tissue morphology was examined and scored blindly scored by an institutional veterinary pathologist. The expression of meprin-1β and p53 in the renal cortex was evaluated using immunohistochemistry and quantitative ROI analysis. Tissues images were analyzed by reporting the area of cells above a set intensity threshold divided by the total area sampled. In addition to the controls listed herein, the contribution from only the secondary antibody was measured.

An evaluation was conducted of progression-free survival in mice that were prophylactically treated to silence the renal expression of p53 and meprin-1β, in anticipation of a scheduled nephrotoxic dose of cisplatin, to test the medicinal utility of f-CNT-mediated RNAi. Over a 5 day period, each animal received a daily dose of 1.6 mg f-CNT+0.087 mg siRNA per kg (1:1 mol/mol) or 0.087 mg siRNA per kg or PBS vehicle in 0.100 mL by IV injection. On day 3, a single IP dose of cisplatin (Sigma, 10 mg/Kg in NSS) was administered. In this study 8 groups of female balb/c mice (10-12 month old) were arranged as follows: (a) PBS vehicle (n=5); (b) f-CNT/siMep1b (n=8); (c) f-CNT/siTrp53 (n=8); (d) f-CNT/siScram (n=8); (e) siMep1b (n=8); (f) siTrp53 (n=8); (g) a combination of f-CNT/siMep1b/siTrp53 (n=8); and (h) a combination of siMep1b/siTrp53 (n=8). Blood samples from each mouse were collected on days 0, 1, 5, 8 and 11 (from cisplatin administration); weights were recorded daily; and observations of activity were noted. Mice were sacrificed at day 14 and kidneys were collected, fixed and embedded in paraffin for histological studies. Progression-free survival was analyzed using the Kaplan-Meier method to score outcomes of weight loss (>20% of initial mass), renal biomarker values (>3 standard deviations relative to untreated group mean), severe lethargy or death. The 10 mg/Kg cisplatin dose was selected for use in these mice to produce a nephrotoxic insult and was determined based on a dose response study that measured renal damage biomarkers and survival as a function of time from administration.

A dose response experiment was performed to assess nephrotoxicity in Balb/c mice. Mice were weighed and then administered an IP injection of different doses of cisplatin (Sigma) in NSS (0, 7.5, 15, 22.5 and 30 mg/Kg). Blood was collected at 24 h post-injection to assess changes in BUN, serum creatinine, phosphorous and magnesium relative to control animals.

Cisplatin nephrotoxicity in Trp53 null mice was studied using female C57BL/6 p53-null (n=5) and wild-type (n=5) mice which received a 22.5 mg/Kg IP dose of cisplatin in NSS. Untreated controls (n=5 mice per group) received only IP injections of NSS. BUN and serum creatinine biomarkers were assayed at 24 h post-administration.

Data Analyses

Three-dimensional region-of-interest analysis on PET images was performed with AsiPRO VM 5.0 software (Concorde Microsystems). Widefield and confocal microscopy images were evaluated using ImageJ (NIH, http://rsb.info.nih.gov/ij/), AxioVision LE (Zeiss), and Amira 4.1 (Visage Imaging, Inc.) software. Graphs were constructed and statistical data were evaluated using Graphpad Prism 3.0 (Graphpad Software, Inc.). Statistical comparison between 2 experimental groups was performed using a t test (unpaired comparison).

Incorporated herein by reference are all protocols and methods disclosed in Ruggiero A, et al. (2010) Paradoxical glomerular filtration of carbon nanotubes. Proc Natl Acad Sci USA 107(27): 12369-12374; McDevitt M R, et al. (2007) PET imaging of soluble yttrium-86-labeled carbon nanotubes in mice. PLoS One 2(9):e907; Ruggiero A, et al. (2010) Imaging and treating tumor vasculature with targeted radiolabeled carbon nanotubes. Int J Nanomedicine 5:783-802.

Example 2: Kinetics of F-CNT-Mediated siRNA Transport In Vitro

The kinetics of cellular internalization of the 1:1 complex were investigated with HeLa cells that expressed EGFP (EGFPHeLa) using time-lapse confocal microscopy and a cyanine dye-siRNA construct (siEGFP-Cy3). The EGFP+ HeLa cells were exposed to a 50 nM concentration of f-CNT/siEGFP-Cy3 (1:1) and internalization was imaged as a function of time. In accordance with a loading and off-loading mechanism, the molecular f-CNT/siEGFP-Cy3 assembly did not fluoresce upon excitation (due to the quenching of the cyanine emission by the f-CNT). The siEGFP-Cy3 began to dissociate from f-CNT and Cy3 emission was detected at 2h and peaked at 5h as the f-CNT/siEGFP-Cy3 was internalized and diluted intracellularly (relative to the initial concentration of the f-CNT/siEGFP in the extracellular milieu). The siEGFP-Cy3 alone exhibited negligible internalization. This dynamic fluorescence microscopy result underscored the importance of the f-CNT as an efficient delivery vehicle and validated a concentration-based off-loading mechanism.

This kinetic result was confirmed with a radioassay that measured f-CNT/siEGFP-[$^{111}$In]DOTA internalization in the EGFP+HeLa cell system. Cellular internalization occurred 1-3h post-transfection and the f-CNT-mediated siEGFP-[$^{111}$In]DOTA uptake was greater than the cellular uptake of siEGFP-[$^{111}$In]DOTA alone (control) for all time-points. This radioassay permitted quantification of the mass of siEGFP delivered by f-CNT to the cell based upon the specific activity. Accordingly, approximately $10^4$ molecules of siRNA were delivered by f-CNT per cell versus minimal uptake in the control.

Figure 1B:
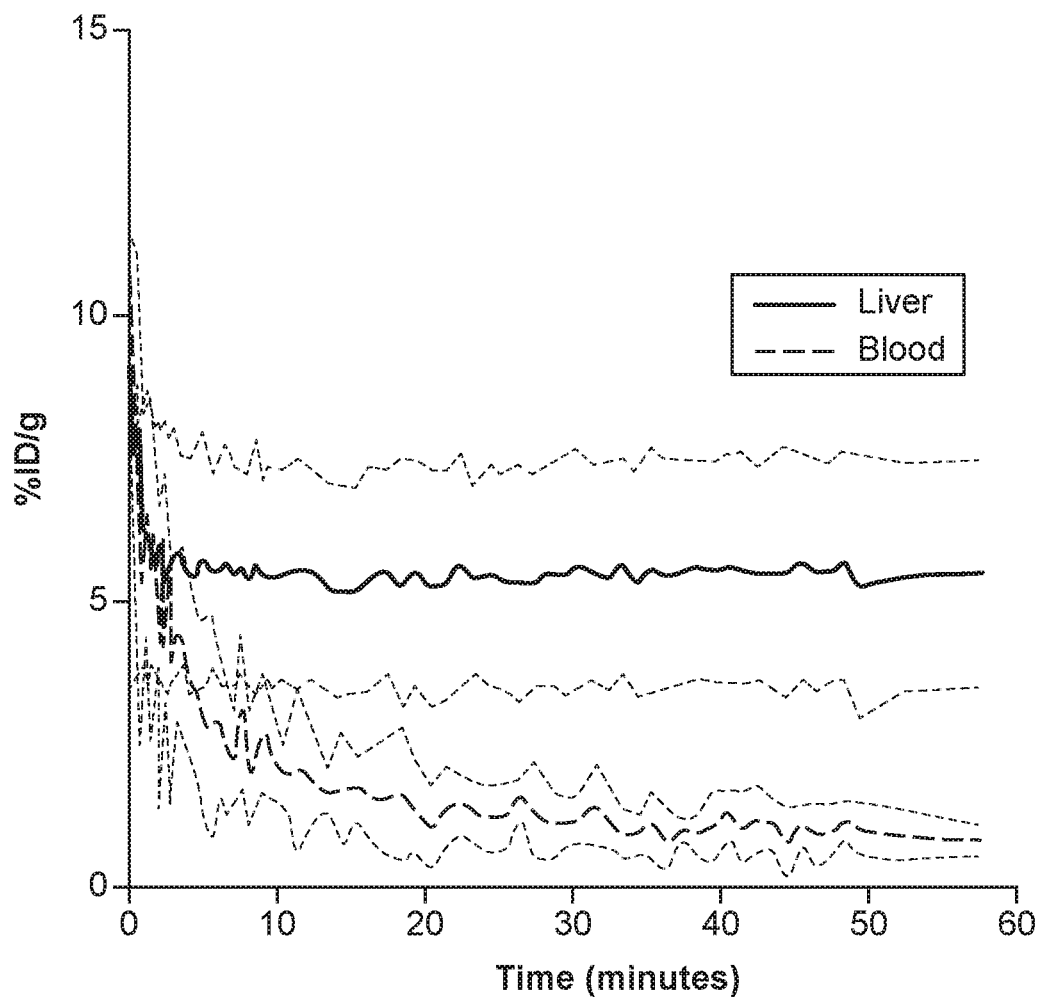
Figure 1C:
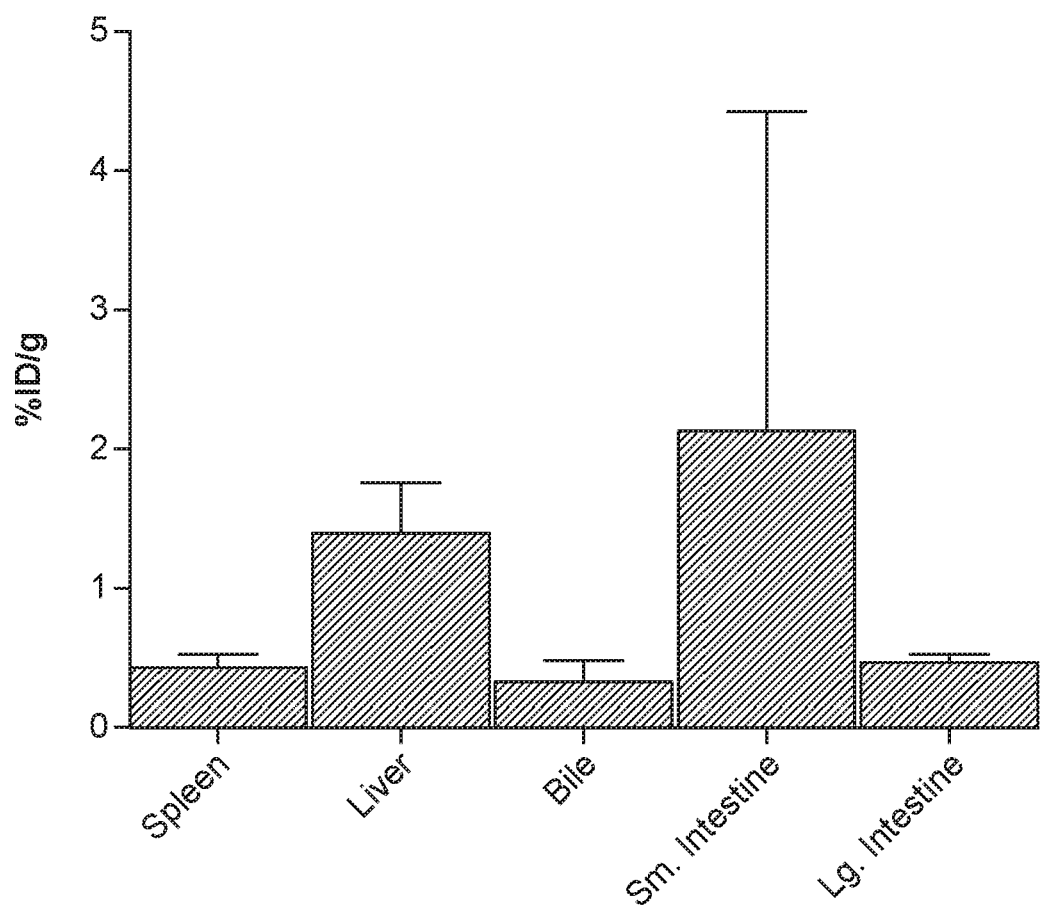
Figure 1D:
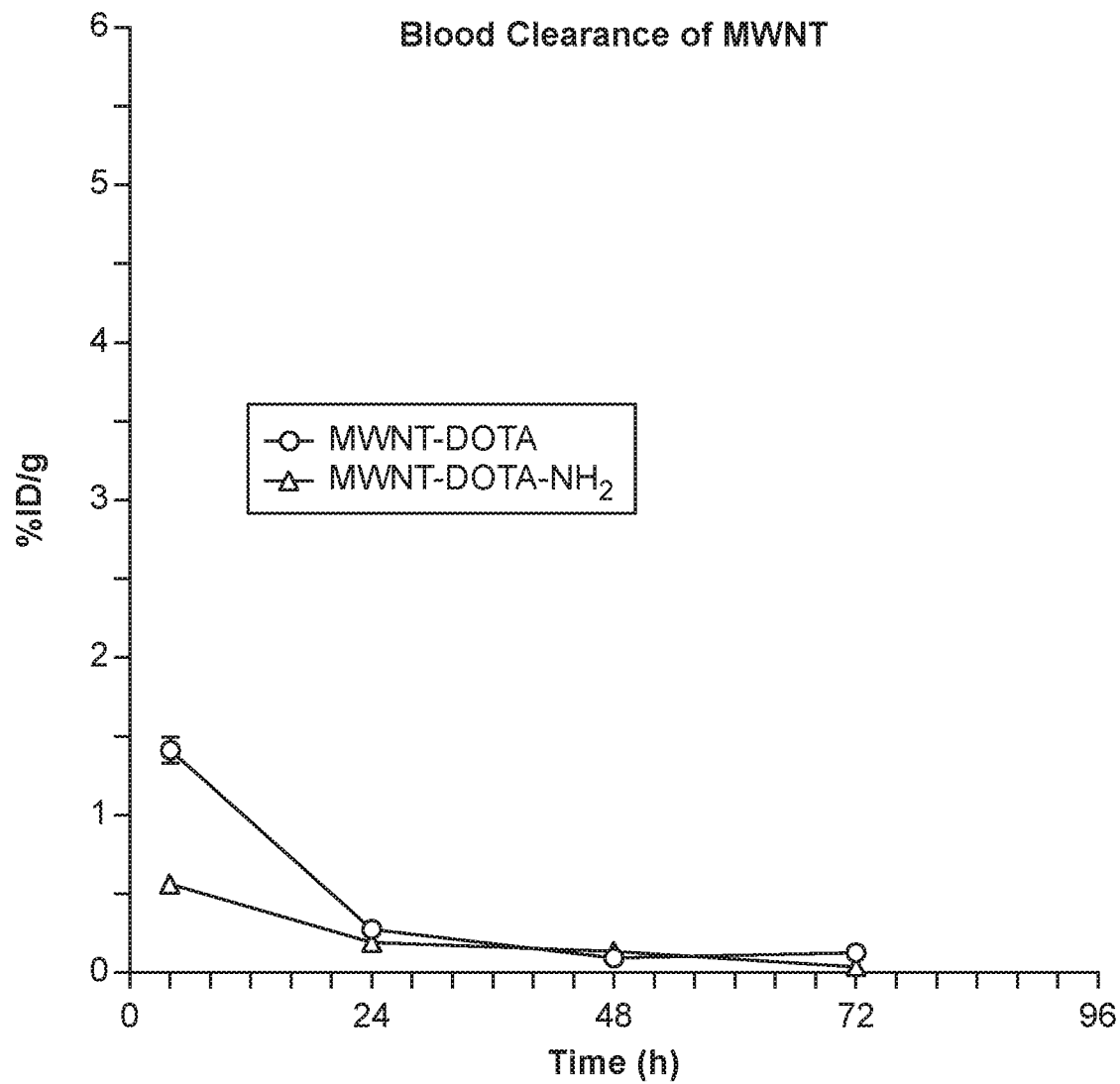
FIG. 1D shows time-activity curves generated from region-of-interest analysis (% injected dose (ID)/g) of blood compartment clearance for multi-walled carbon nanotubes.
Figure 1E:
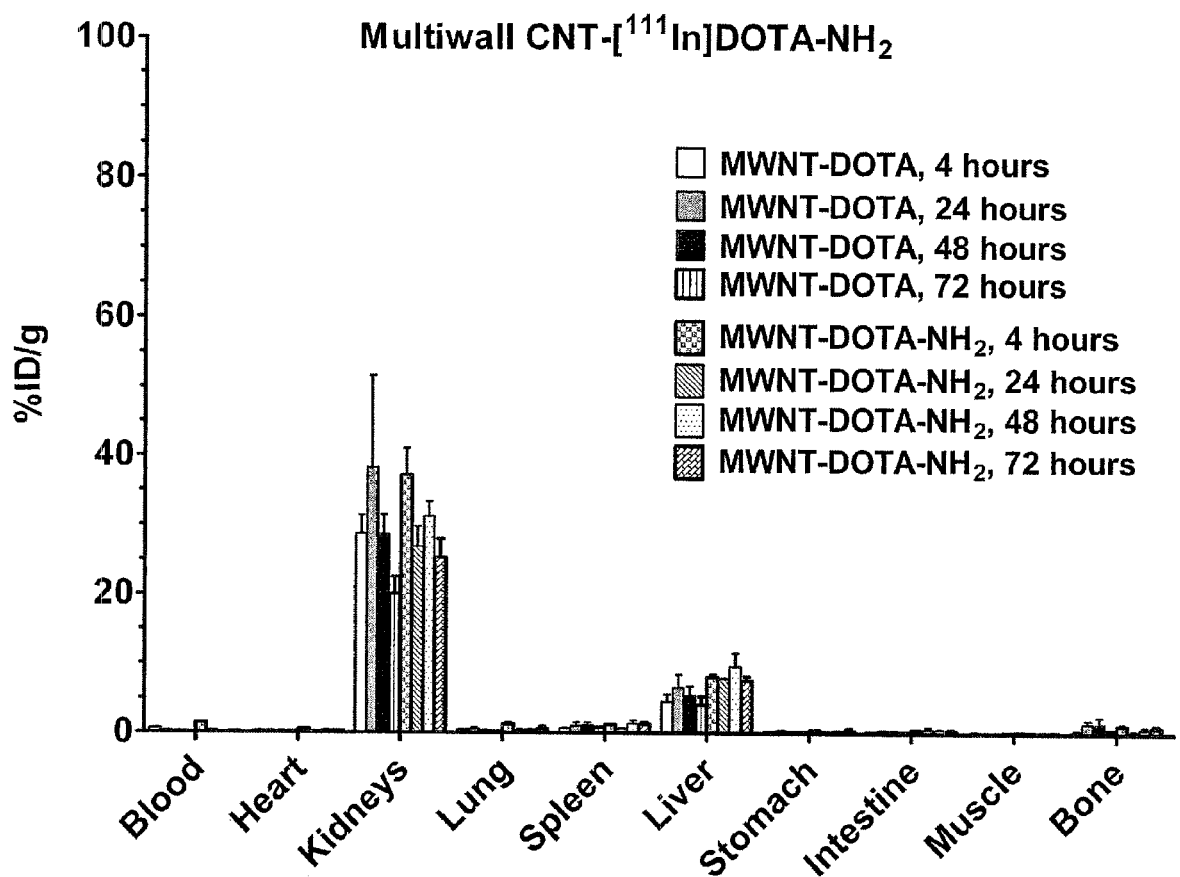
FIG. 1E shows biodistribution of multi-walled carbon nanotubes in select tissue (% ID/g).

A macromolecular singled-walled carbon nanotube-[(DOTA)(AF488)(AF680)] nanomaterial (f-CNT) was used to describe renal distribution and glomerular filtration and to probe hepatic processing of f-CNT. This nanomaterial was designed to investigate the global (whole body), local (liver), and cellular PK profile in an animal model and report its location via multiple imaging modalities.

f-CNT was prepared from amino-functionalized single-walled carbon nanotubes that have been further functionalized with multiple copies of fluorescent dyes and metal-ion chelates; radiolabeled with yttrium-86 (86Y; 3+; t1/2=14.7 h) or indium-111 ($^{111}$In; γ; t1/2=2.81 d) and characterized before and after injection into mice. The f-CNT is assayed to contain 0.02, 0.04 and 0.4 mmol of AF488, AF680 and DOTA per gram of single-walled carbon nanotubes, respectively. Representative constructs (L-300 nm; MW-300 kD) would display 7-10 AF488, 14-20 AF680, and 140-200 DOTA moieties per f-CNT. [$^{86}$Y]f-CNT had a specific activity of 322 GBq/g (8.7 Ci/g) and was 296% radiochemically pure. Multi-walled carbon nanotubes and any fibrillar molecule (aspect ratio greater than 1) can also be used (FIGS. 1D-E). See Scheinberg D A, Villa C H, Escorcia F E, McDevitt M R. "Carbon Nanotubes" In: *Drug Delivery in Oncology, From Basic Research to Cancer Therapy,* 3 Vol., Kratz, Senter, and Steinhagen (editors) Wiley-VCH, Weinheim, Germany (2011) pp. 1163-1185. ISBN: 978-3-527-32823-9.

The PK profile of the construct was determined with i) dynamic positron emission tomography (PET) imaging; ii) tissue and fluid harvest of the entire animal; and iii) immunofluorescence (IF) staining and microscopy of the liver to mark f-CNT location. IF co-staining serves to identify and demarcate specific hepatic cell populations and associated organelles that process the f-CNT.

f-CNT rapidly cleared the blood with a small fraction accreted in the liver or transported via the bile into the gall bladder and subsequently the lower alimentary canal for elimination. Dynamic PET imaging, tissue biodistribution, and chromatographic analysis of bile were performed to investigate the whole body PK profile in a naïve animal model. The whole body projection image for a representative mouse showed that the activity in the vascular compartment was cleared by 60 min. and revealed high contrast images that emphasized only minimal tissue (kidney, liver and spleen) activity.

The majority of the injected activity (~80-85%) was rapidly eliminated in the urine as determined by bladder imaging. The f-CNT demonstrated rapid blood clearance, predominantly renal elimination (urine), and localization of only a fraction of the injected dose in the liver, kidneys and spleen within 1 hour post-administration. Time-activity curves for blood and liver (FIG. 1B) graphically showed the rapid clearance from the blood compartment (t1/2-6 min.) and the swift accumulation of a fraction of the injected dose (ID) in the liver. Biodistribution experiments (FIG. 1C) measured the % ID that partitioned into the blood, tissue, and bile as a function of time. Activity was measured in the liver (1.39±0.39% ID/g), bile (0.35±0.15% ID/g) and small intestines (the duodenum, jejunum, and ileum contained 2.17±2.31% ID/g) at 1 h. The liver had 2.26±1.78% ID/g and the bile had 0.22±0.16% ID/g at 3 h. The activity eliminated via the alimentary canal was in feces by 24 h as determined by activity counts.

Intact f-CNT was transited into the gall bladder as shown using radiochromatographic analysis of the radioactivity (eluted at 13-15 min.) that collected in the bile. Control experiments examined an external physical mixture of the radiolabeled f-CNT with bile removed from a naïve animal which exhibited the same retention time (13-15 min.). Little-to-no activity was observed in the bile of control mice that were injected with only [$^{111}$In]DOTA and suggested that renal clearance was preferred for this small molecule. A further control verified that the radiolabeled chelate was still attached to the f-CNT as only the [$^{111}$In]DOTA component (externally mixed with naïve bile) eluted at an earlier time (8-9 min.) in the reverse phase method.

The f-CNT that accumulated in the liver was not in the hepatocytes, rather, it was limited to cells residing in the sinusoidal space. IF microscopy revealed that f-CNT was localized exclusively in the hepatic sinusoids, associated with small nucleated cells lining the sinusoids. f-CNT was visualized using anti-AF488 staining that was directed at the AF488 moieties covalently appended onto the SWCNT sidewall (FIG. 1A). This anti-AF488 probe was multiplexed with 4',6-diamidino-2-phenylindole (DAPI) stain and an array of appropriate co-stains selected to classify distinct cell types and organelles. The absence of f-CNT in the HC population was corroborated with N-cadherin staining which delineated the HC plasma membrane. Once the f-CNT cleared the blood compartment there were no changes in tissue distribution observed as a function of time.

The two experimental controls included mice that were injected with only AF488 and a mouse that received only the injection vehicle; neither control liver section stained with anti-AF488. Additionally, a fraction of f-CNT that entered the liver, but did not localize in the hepatic sinusoid, was found intact in the bile and subsequently in the intestine (FIG. 1C). However, the f-CNT that was eliminated intact via the bile was not localized to the BDEC that provided the conduit to the gall bladder.

Liver sinusoidal endothelial cells (LSEC) localized the f-CNT which was compartmentalized in the lysozomes and Golgi apparatus. The discontinuous LSEC that line the hepatic sinusoids were the predominant cell type that localized the f-CNT as confirmed by multiplex IF detection with CD31, Lyvel, anti-AF488, and DAPI stained liver sections. CD31 is a pan-endothelial marker and Lyvel is a marker for lymphatic endothelial cells with the LSEC being a notable exception. The CD31 and Lyvel cell membrane markers entirely circumscribed the anti-AF488 signal, substantiating f-CNT uptake into the LSEC population. In some of these cells, the punctuate anti-AF488 staining pattern was associated with both Lamp2 stained lysozomal and GM130 stained Golgi compartments. Continuous VE constituting the rest of the liver vasculature did not show any accumulation of the f-CNT and called attention to the differential capacities of specialized discontinuous LSEC and continuous VE to accumulate and internalize f-CNT. Liver sections stained with MECA32, another VE cell marker, confirmed this finding.

The Kupffer cells (KC; predominant liver macrophages) did not accumulate f-CNT to any extent. Surprisingly, KC engulfment of f-CNT was very rarely observed in IF images of the liver sinusoid. These data were generated by multiplex IF staining directed against the AF488, CSF-1R, and DAPI. This result was confirmed using Iba-1, another macrophage marker. In addition, 3-dimensional images confirmed the absence of anti-AF488 and CSF-1R co-localized signal in the sinusoid.

Stellate cells only rarely accumulated f-CNT. The SC population in the liver perisinusoids was mapped with GFAP. Only a very infrequent co-localization of anti-AF488 and GFAP was observed as compared to the LSEC. Images employing anti-AF488, DAPI, Lyvel, and GFAP only rarely showed f-CNT and SC association but demonstrated predominant LSEC accumulation.

Splenic cell accumulation of f-CNT paralleled hepatic localization. Biodistribution studies showed that the spleen was another site of f-CNT uptake (<1% ID/g) (FIG. 1D). Splenic tissue sections from mice injected with f-CNT stained positively for AF488 versus tissue from a control animal that received only AF488. IF imaging analyses showed that f-CNT accumulated in the specialized splenic sinusoidal endothelium (SSEC) using β-catenin and CD31 stains. 3-D images confirmed the co-localization of f-CNT and SSEC in the splenic sinusoid. The splenic macrophage (SM) population (stained with Iba-1) did not accrete f-CNT.

This profile paralleled the cytodistribution observed in the liver.

Nanoparticles, in general, are severely limited by untoward hepatic uptake and lack of renal clearance. While the bulk of f-CNT are renally cleared, the next most prominent organ contributing to their clearance is the liver. However, the hepatic PK data reported herein showed the surprising result that f-CNT either accumulated chiefly in LSEC (professional endothelial scavengers) or cleared intact by hepatobiliary elimination. The liver biocompatibity of these nanomaterials is now explained by a combination of specific and efficient LSEC scavenging and intact biliary clearance.

The various nonparenchymal cells that populate the liver sinusoid are interleaved and difficult to distinguish. Multiple IF stains differentiate between KC, LSEC, and SC. The data demonstrated that most of the f-CNT was scavenged by LSEC, presumably because this nanomaterial behaved like a macromolecule rather than a large particulate which were expected to be phagocytosed by KC. The presumed KC opsonophagocytosis of single-walled carbon nanotubes was not observed with this f-CNT as determined using discreet cell markers to unequivocally identify phenotype. The lack of definitive evidence of KC uptake may well reflect the distinct physicobiochemical properties of this covalently modified f-CNT versus non-covalently modified single-walled carbon nanotubes (e.g., dispersed with a surfactant or polyethylene glycol). Non-covalently modified single-walled carbon nanotubes exhibited only a brief half-life (minutes) in the blood before displacement of the solubilizing agent by serum proteins. The downside to such non-covalent dispersal was that the nanocarbon construct was inherently unstable and aggregated, rendering it susceptible to macrophage opsonophagocytosis. In addition, since the surfactant dispersed materials were unable to efficiently clear renally, a greater majority of the injected dose was accumulated in liver, as compared to f-CNT that was rapidly renally filtered and exhibited only minimal accumulation in liver and spleen. This shows that macromolecular f-CNT remain soluble and individualized.

The vascular endothelial termini in the liver, spleen and marrow are tortuous sinusoids. The hepatic sinusoids interface between the blood supply and the HC and mediate scavenging and transport of blood-borne solutes. These LSEC exhibit a discontinuous endothelium possessing numerous open fenestrae, without diaphragm or basement membrane. This sieve plate morphology and high endocytic capacity of LSEC support their unique role in solute trafficking and active scavenging of macromolecules and colloids that would escape KC phagocytosis. The punctuate staining pattern of f-CNT in LSEC was shown by lysozome- and Golgi-compartmentalized nanocarbon. Approximately 0.26% of the cells in the porcine liver are LSEC. Assuming a similar ratio for mouse liver, our biodistribution data indicated that only 3E6 LSEC accumulated 3% ID; further if 3% ID was 1E-12 moles f-CNT (6E11 molecules), then each LSEC scavenged approximately 2E5 f-CNT molecules. Therefore, a relatively small number of LSEC have a high capacity to rapidly eliminate these macromolecules (at mg/L concentrations) from the blood. However, considering their location in the hepatic architecture, they were well-positioned to intercept and efficiently capture the f-CNT.

Stellate cells reside in the hepatic perisinusoidal space of Disse intimately positioned between LSEC and HC. The paracrine secretion of VEGF by SC sustains the LSEC population and promotes autocrine production of NO by LSEC. SC also store retinoids as retinyl palmitate in cytoplasmic globules. The HC hydrolyze retinyl esters to retinol that is then transported into SC as a complex with retinol-binding protein. It has been shown that LSEC play an important role in maintenance of SC quiescence and prevent their activation and loss of the VEGF paracrine effect. While LSEC were the predominant target for f-CNT, there was occasional evidence of f-CNT in SC. Because one function of the LSEC is to guard the SC and prevent activation, it was evident that a small amount of f-CNT was not scavenged and instead taken-up by the SC.

The continuous VE architecture served as the primary conduit to distribute f-CNT in vivo but there was no evidence that it accumulated this nanomaterial. This called attention to the differential functionality of these two endothelial cell types with continuous (VE) or discontinuous (LSEC) cytoplasm. Cultured endothelial cells were observed to accumulate SWCNT, albeit under non-physiologic conditions over a prolonged time, however, our PET imaging and IF studies have not tracked any f-CNT to the continuous VE.

A small fraction of intact f-CNT cleared the liver via secreted bile and was harvested downstream in the gall bladder and assayed. The presence of activity in the bile, intestines and feces strongly supported the role of hepatobiliary clearance of f-CNT. The BDEC that comprise these ducts did not show any f-CNT accretion. Some of the f-CNT in the sinusoid may be actively endocytosed by the LSEC and another portion diffused from the Disse space into the biliary canaliculi and subsequently into the bile. Because no evidence was observed of accumulation of f-CNT in HC and the bile contained intact nanomaterial, it was difficult to reconcile a mechanism whereby the HC mediated transport of f-CNT from blood to bile. Evidence for a permeable barrier permitting bile pigments and cellular debris to bypass HC processing and transit directly from blood to bile has been reported and scanning electron microscopy has shown 100 nm zones between the space of Disse and the bile canaliculi that were interpreted as sites for molecular diffusion. These permeable Disse/canalicular junctions may be utilized to effect retrograde, non-viral gene therapy to the liver via infusion from the biliary tree. The conventional view of HC-mediated elimination of blood-borne solutes into bile overlooks this unexpected diffusion process.

Figure 1F:
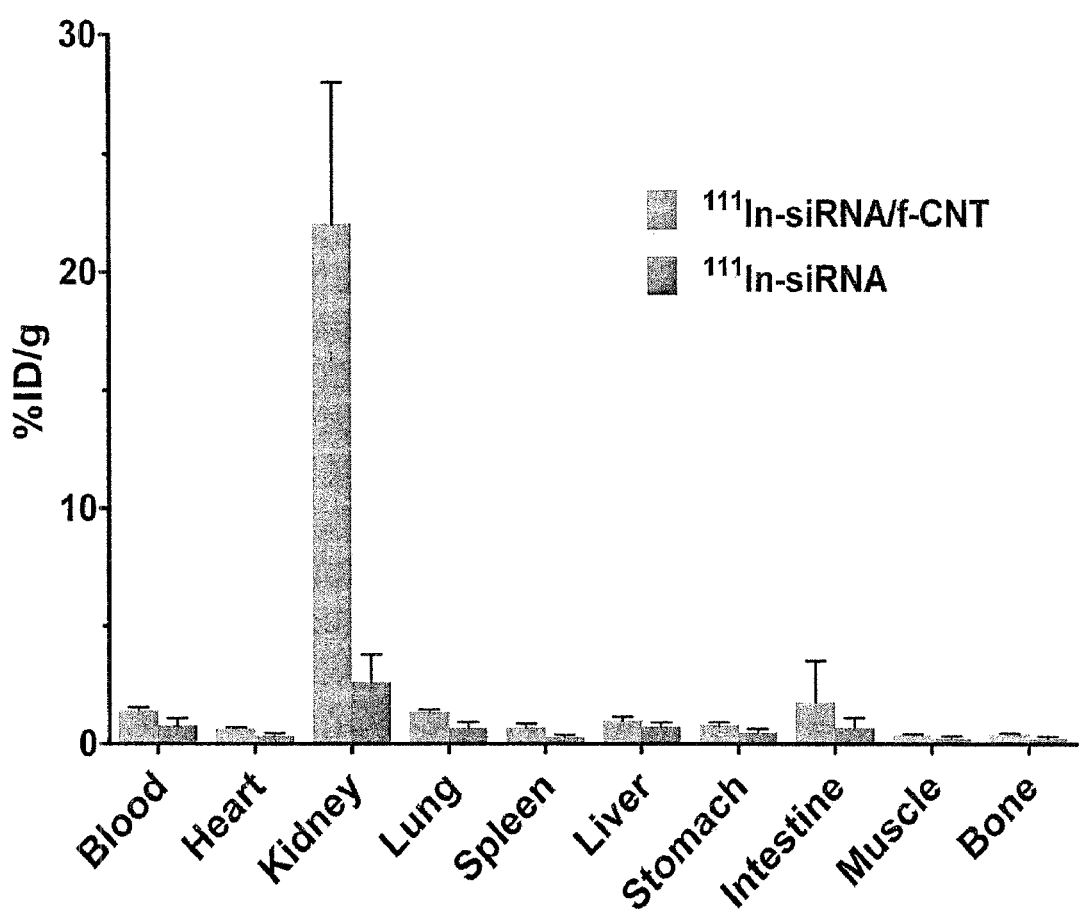
FIG. 1F shows biodistribution of siRNA/f-CNT in select tissue (% ID/g).

The spleen was also evaluated for f-CNT uptake and accumulated only a small amount of activity (<1% ID/g). Unexpectedly, f-CNT partitioned into the SSEC and eschewed SM uptake. The splenic sinusoids are tortuous VE termini lined with specialized SSEC. The SSEC differ from LSEC in that they exhibit continuous cytoplasm and disorganized basement membrane. The spleen is another important reticuloendothelial tissue and it paralleled the liver in the cell types that localized f-CNT. Significant biodistibution of siRNA/f-CNT to the kidney versus siRNA alone was observed (FIG. 1F).

Renal clearance remained the primary route of intact elimination and accounted for approximately 80-85% of the excreted f-CNT while the hepatobiliary clearance route was a secondary route and accounted for approximately 3-5% of the excreted f-CNT.

The predominant hepatic cell type that accumulated fibrillar nanocarbon was a professional scavenger that performed rapidly and at high capacity. The fraction of f-CNT that transited the liver, but was not scavenged, underwent biliary elimination. These findings in conjunction with the known renal processing and elimination of f-CNT accounted for elimination of approximately 90% of the injected dose. Mouse LSEC have 14±5 fenestrae per µm2 (humans have 15-25 per μm2) with diameters of 99±18 nm (humans, 50<d<300 nm). This is an avid, dedicated mammalian scavenger cell and in combination with intact biliary elimination of f-CNT has yielded a very favorable biological outcome in animal models. This profile can be extrapolated to humans assuming proportional LSEC capacity and capability. Biocompatibility has always been observed with similarly modified non-toxic f-CNT in animal models. These findings give explanation of the action of the host on the f-CNT and support use in man. These findings indicate that the complete pharmacokinetic profiles of other nanoparticles can be revealed using the same paradigm employed herein to analyze this fibrillar nanocarbon.

Example 3: EGFP Silencing by Delivery of siRNA Linked to f-CNT

Green fluorescent protein (GFP) is a protein that exhibits bright green fluorescence when exposed to light in the blue to ultraviolet range. GFP has a beta barrel structure with eleven β-sheets with six alpha helix(s) enveloping a covalently bonded 4-(p-hydroxybenzylidene)imidazolidin-5-one chromopore. A folding efficiency point mutation to this structure yields enhanced GFP (EGFP).

The f-CNT-mediated delivery of siRNA that targeted green fluorescent protein was first evaluated in EGFP$^+$HeLa cells as a proof-of-concept in vitro. Time-lapse confocal microscopy images were collected over 60h and region-of-interest (ROI) analyses showed that f-CNT/siEGFP and a Lipofectamine/siEGFP (Lf/siEGFP) positive control produced a significant decrease in HeLa cell fluorescence, while the siEGFP alone control was less effective. Several cycles of cell division were imaged during the course of the experiment and confirmed both cell viability and biocompatibility of the f-CNT transfection reagent. The f-CNT-mediated siEGFP expression was reduced 70% at 24h and 92% at 60h ($P<0.0001$) and more significant than the control siEGFP alone at 60h ($P=0.0003$).

Confirmation of EGFP interference was obtained using flow cytometry, Western blot analysis, and RT-PCR. Each method demonstrated a decrease in either EGFP protein or gene expression for the f-CNT-mediated RNAi compared to control groups. Flow cytometry confirmed that f-CNT/siEGFP yielded a 2-log greater fluorescence shift of EGFP expression compared to controls and was also more effective than Lf-mediated interference. Western blots demonstrated a reduction of EGFP expression after f-CNT/siEGFP treatment compared to controls. RT-PCR data showed a significant effect of the f-CNT/siEGFP compared to the controls; a kinetic analysis indicated that the maximum mRNA interference occurred on day 2. The cytotoxicity of the nanocarbon vector was evaluated with HeLa cells by flow cytometry as a function of increasing dose of f-CNT (or controls) for 3d with no significant toxicity observed.

Specific renal targeting of f-CNT/siRNA was substantiated by evaluating the PK fate of f-CNT/siEGFP-[$^{111}$In] DOTA in naïve balb/c mice. The kidneys accumulated 9.67+2.58 percent of the injected dose (% ID) of f-CNT/siEGFP-[$^{111}$In]DOTA within 1 h and were the principal tissue targeted. This result correlated with previous f-CNT PK data and indicated that the siRNA vector remained bound to the f-CNT in vivo. Carbon nanotube-mediated delivery resulted in a 10-fold increase of siRNA delivered to the kidneys compared to control ($P=0.0001$). The fraction of dose that was not delivered to the kidney was rapidly (<1 h) eliminated. The differential excretion between the two groups was significant ($P=0.0128$) and a mass balance was accounted for by the preferential renal accumulation of the f-CNT/siEGFP-[$^{111}$In]DOTA. Radio-HPLC of urine samples revealed that the retention time of the f-CNT/siEGFP-[$^{111}$In]DOTA-treated group was the same as the injected formulation and confirmed that the siRNA cargo was protected from serum degradation by f-CNT. Conversely, the urine collected from animals that received the siEGFP-[$^{111}$In]DOTA-only showed a very different retention time compared to the injected formulation. Control experiments with RNAse added to siEGFP-[$^{111}$In]DOTA implicated degradation of the unprotected siRNA in vivo.

A fraction of glomerular-filtered f-CNT rapidly (<5 min.) accumulated in the PTC brush border and transited into the cytoplasm. PTC organelle trafficking was investigated using confocal microscopy. The early-endosome, Golgi apparatus, and lysosomes were identified with EEA-1, GM130, and LAMP co-staining, respectively. Representative images of the early endosome, Golgi and lysosomes all co-stained for AF488; and as expected, the early endosome signal was evidenced earlier (5 min.) and the Golgi and lysosome staining was more pronounced later (1h). This data supports a clathrin-mediated endocytic uptake mechanism for f-CNT internalization by the PTC.

Nanocarbon-mediated interference with a specific gene in the kidney was demonstrated using an actin-promoted EGFP transgenic mouse model treated with the siEGFP sequence. Mice given f-CNT/siEGFP showed a distinct decrease in renal cortical green fluorescence versus the PBS, siEGFP alone, or f-CNT/siScram controls. Individual renal cell fluorescence was quantified and showed a significant decrease in EGFP-expressing cells in animals treated with the f-CNT/siEGFP ($P<0.0001$) compared to controls. Quantitative analysis of the fluorescence in the PTC showed a decrease of about 75% of cells with observable green fluorescence, whereas no significant difference was noticed in the control groups. The morphology of the tubules were indistinguishable (7-8 cells per tubule) and decrease in number of fluorescent cells was the only observable change in the f-CNT/siEGFP treated mice. A Western blot analysis confirmed f-CNT-mediated knock-down of EGFP. It is worthy of note that the untargeted renal vascular endothelial and medullar cells still maintained EGFP expression because they were not targeted.

Example 4: f-CNT-Mediated CTR1 Knockdown Reduced Renal Copper Uptake

Ctr1 is a transmembrane protein responsible for the cellular uptake of copper and is expressed in human heart, kidney, muscle and brain; in the kidney, Ctr1 is specifically expressed in the PTC. Ctr1 has also been implicated as the key mediator of cisplatin uptake into the renal tubule, the accumulation of which leads ultimately to AKI during cancer therapy. Three groups of mice were treated for 3 days with f-CNT/siCtr1, siCtr1 alone, or PBS (daily doses were 1.6 mg f-CNT+0.087 mg siRNA per kg). After the last RNAi treatment, each animal received $^{64}$CuCl$_2$ and the accumulated activity in the kidneys was determined. The f-CNT/siCtr1 group showed a significant decrease in renal copper uptake compared to the untreated group ($P<0.0001$) and the siCtr1 alone ($P=0.0016$). siCtr1 cargo administered without f-CNT transport was unable to significantly decrease copper uptake versus PBS control ($P=0.2757$). Progression-free survival was analyzed using the Kaplan-Meier method and mice had a median time to injury of 4 d.

Figure 2:
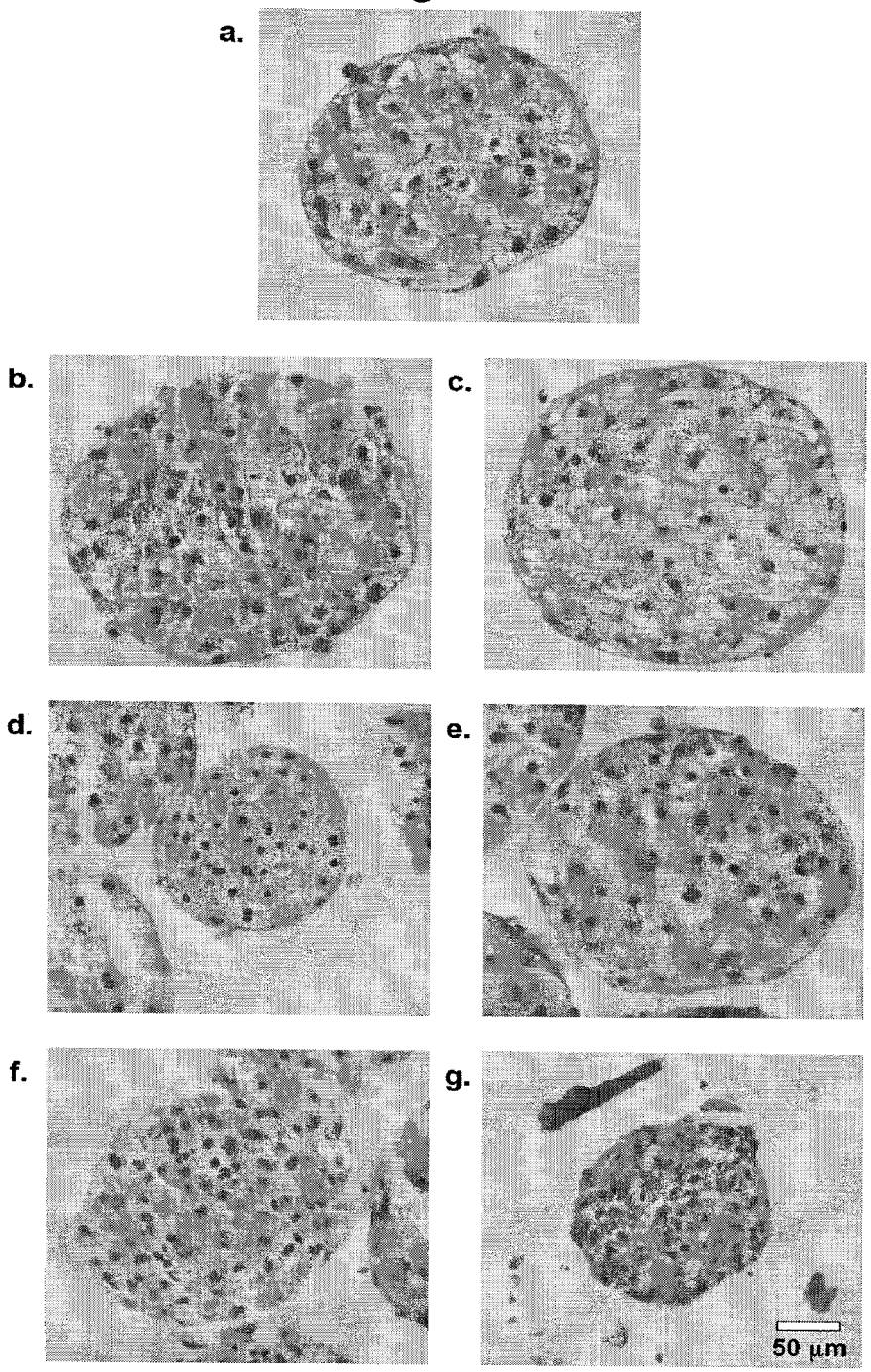
FIG. 2 shows that f-CNT is biocompatible and non-toxic to human liver tissue. Organoids of human liver tissue (microspheres) were exposed to (Panel a) only growth media (untreated control) for 1 d; and to fCNT at (Panel b) 15 mg/L for 1 d; (Panel c) 30 mg/L for 1 d; (Panel d) 15 mg/L for 2 d; (Panel e) 30 mg/L for 2 d; (Panel f) 15 mg/L for 3 d; and (Panel g) 30 mg/L for 3 d. The scale bar applies to all images in the figure. Note that animal studies in vivo administered 0.01 to 0.04 mg/L to mice with most of the dose eliminated in less than 1 h by renal or hepatic clearance. There was no evidence of toxicity to human liver tissue in vitro or mouse liver tissue in vivo.

Example 5: PK Profile of f-CNT in a Non-Human Primate Model and Non-Toxicity of f-CNT in Human Liver Tissue The PK profile of [$^{86}$Y]f-CNT was determined in a naïve non-human primate model using positron emission tomography-computed tomography (PET/CT) imaging. The nanomaterial exhibited similar tissue blood clearance, biodistribution, and renal elimination in a 5 kg cynomolgus monkey (Macacafascicularis) as compared to 20 g murine models. A 1 mg/kg dose of [$^{86}$Y]f-CNT was administered intravenously and had a blood half-life of 7 min. The majority of the dose was rapidly eliminated in the urine with a fraction accumulated in the kidneys (SUV was 16). Furthermore, f-CNT was found to be biocompatible and non-toxic to human liver tissue in vitro (FIG. 2, Panels A-G).

Example 6: Delivery of siRNA Linked to f-CNT as a Prophylaxis Against Acute Kidney Injury Two key proteins were selected as targets in our study because of their involvement in the progression of AKI. Meprin-1β and p53 have key roles in the depolarization and apoptotic processes of kidney injury and their mRNA was targeted using the f-CNT platform to mediate siRNA delivery. Theses preliminary experiments (i) established the ability of f-CNT to deliver the siMep1b and siTrp53 cargoes and interfere with their respective protein expression, and (ii) evaluated the safety of the f-CNT/siRNA doses to be used prophylactically. Mice were grouped as follows: f-CNT/siMep1b; f-CNT/siTrp53; siMep1b; siTrp53; and PBS vehicle. Each animal received the f-CNT/siRNA constructs, the siRNA alone, or the PBS vehicle for 3 consecutive days. The 0.10 nmol dose of the f-CNT/siRNA per mouse was chosen to yield an on-board [f-CNT/siRNA] of approximately 100 nM in order to insure that the construct remained intact until delivered to the PTC. The schedule administered 1.6 mg f-CNT and/or 0.087 mg siRNA per kg body weight per mouse per day.

Figure 3A:
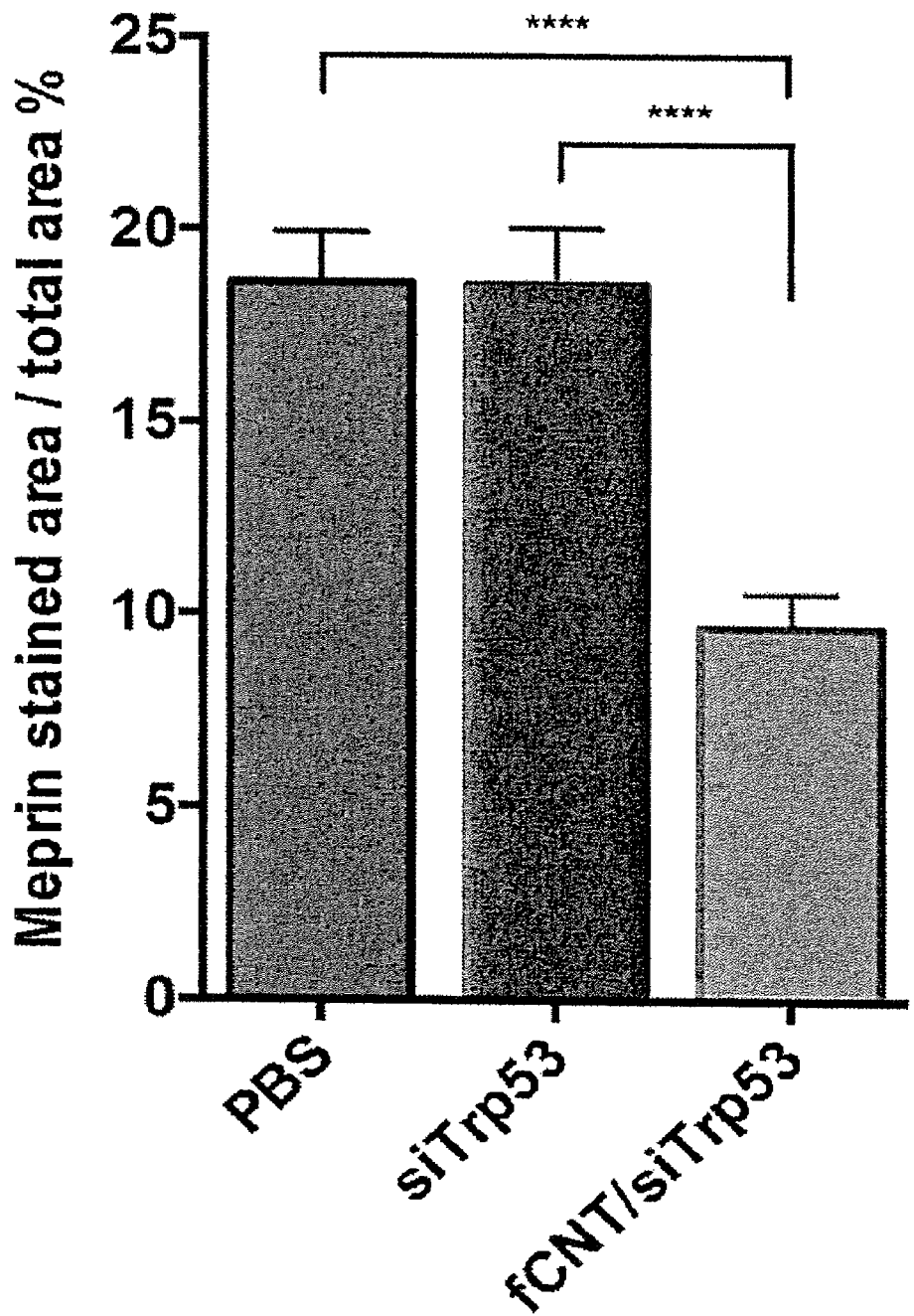
FIGS. 3A and 3B show renal expression of p53 and meprin-1β is reduced by fCNT-mediated RNAi.
Figure 3B:
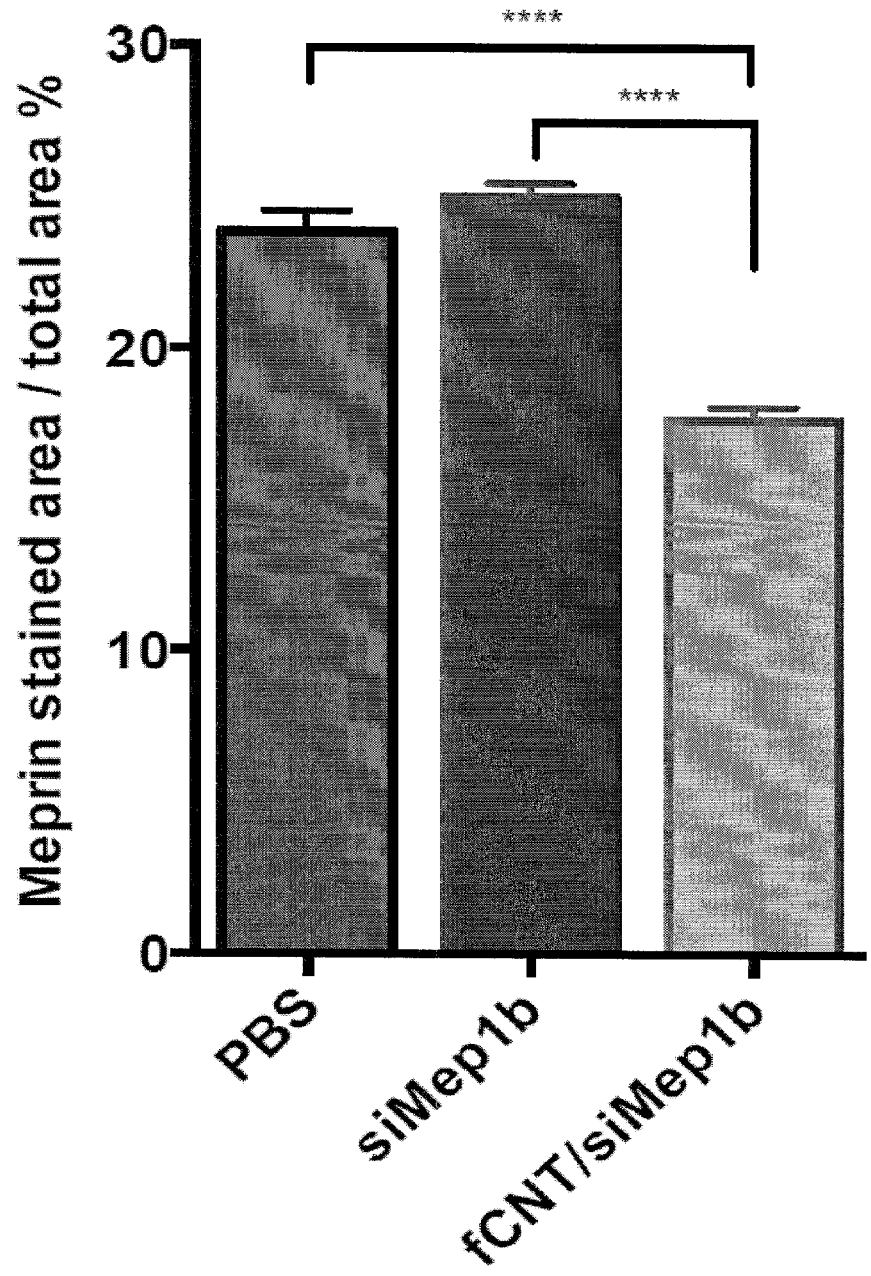

Immunohistochemistry (IHC) and ROI quantification (FIG. 3) showed that the f-CNT-mediated RNAi reduced the expression of the target proteins in the cortex. Basal expression of Trp53 was visibly greater in the vehicle and siTrp53 groups versus f-CNT/siTrp53. Quantitative ROI analysis of these images described a significant decrease in basal Trp53 expression in the f-CNT/siTrp53 group versus Trp53 alone (P<0.0001) and vehicle (P<0.0001) (FIG. 3A). Control staining with only the secondary antibody distinctly demonstrated that it was not contributing to the signal. Similar observations were made in the kidney cortices stained for meprin-1β (FIG. 3B). Basal meprin-1β expression was significantly minimized when mediated by f-CNT versus Mep1b alone (P<0.0001) and vehicle (P<0.0001). Control staining with only the secondary antibody confirmed that it was not contributing to the signal.

These nanocarbon drugs did not adversely affect renal health. Renal function was assessed using a metabolic panel that examined blood urea nitrogen (BUN), serum creatinine (sCr), and phosphorous (P) as biomarkers of kidney injury. No statistical changes were observed for any of the biomarkers indicating that there was no injury arising from the prophylactic nanocarbon or siRNA components. The tissue morphology was examined and scored with no structural abnormalities to report.

A therapeutic strategy relied on simultaneous targeting and down-regulation of meprin-1β and p53 expression in the renal proximal tubule cells. The ability of f-CNT-mediated delivery of a combination of siMep1b and siTrp53 to protect mice from renal injury resulted from mRNA degradation and reduced expression of two proteins that contribute to loss of epithelial cell polarity and apoptosis; the upregulation of either protein can initiate injury. These findings indicate that the loss polarity and apoptosis in PTC were distinct co-events that can each contribute to injury but the co-administration of siMep1b and siTrp53 minimized injury. This strategy focused on early injury events along the pathogenic axis and minimized renal damage, inflammation, and fibrosis. This mechanism is contingent upon the efficient delivery of combination RNAi to the PTC afforded by the f-CNT.

f-CNT are rapidly cleared from the blood compartment and are filtered by the kidneys in animal models. While most of the f-CNT dose was excreted into the urine, a significant fraction of the injected dose (10-15%) was reabsorbed by the renal proximal tubule cells (PTC). The f-CNT have an extremely high aspect ratio (diameter of 1 nm, and a mean length of ~300 nm) and exhibit fibrillar pharmacology. The present method takes advantage of f-CNT fibrillar pharmacology to systematically deliver siRNA to PTCs to silence key genes and minimize nephrotoxicity.

f-CNT can be used to transport, protect, and mediate the specific delivery of small interfering RNA (siRNA) cargo to the PTC in vivo. siRNA vectors can be very strongly bound to f-CNT (Kd~5 nM) under physiological conditions; the supramolecular siRNA/f-CNT construct exhibits the same pharmacokinetic profile as the f-CNT vehicle; and the f-CNT specifically mediated the delivery of siRNA to renal PTC and interfered with the expression of EGFP, SLC3A1, Ctr1, p53, and meprin-3 in vivo. The f-CNT vehicle yields a 10-fold improvement in the systemic delivery of siRNA to the kidney versus siRNA-alone. Furthermore the nanocarbon platform protected the siRNA cargo in vivo as the excreted portion of the siRNA/f-CNT dose was found intact in the urine, but the siRNA-alone control was serum degraded. Post-transcriptional gene silencing of MMP-9, JNK, Epas1, Hif1an, Ac1, Fih1, Irp1, Egln1, Egln2, Egln3, PHD1, PHD2, PHD3, CTR1, CTR2, cFOS, FOS, cJUN, JUN, Fra1, Fra2, ATP, AP-1, MEP1A, MEP1B, VIM, p53, FASR, FASL, COL3A1, Kim-1 and C3 gene expression are all possible via siRNA delivery to kidney cells via single-walled carbon nanotubes.

Nanocarbon-mediated RNAi as a treatment for AKI that transforms the way in which a nephrotoxic renal insult can be managed clinically in order to lessen injury. This f-CNT platform technology has a major clinical impact in the prevention and treatment of AKI as a consequence of the considerable nephron accumulation, minimal off target distribution, rapid clearance of undelivered cargo, and the protective packaging of siRNA. PET/CT data in NHP showed that the f-CNT had similar distribution and clearance in a large animal model compared to rodent models. This parallel PK profile shows that f-CNT will scale similarly to human use. Developing a robust prophylactic strategy to anticipate and minimize AKI overcomes an unmet medical need. The application of this approach to a large at-risk patient population will have a broad and significant impact in health care. Moreover, this technology serves as a precision tool in the study of biological pathways in the nephron and aids in selecting appropriate targets to facilitate the drug design process.

Figure 4A:
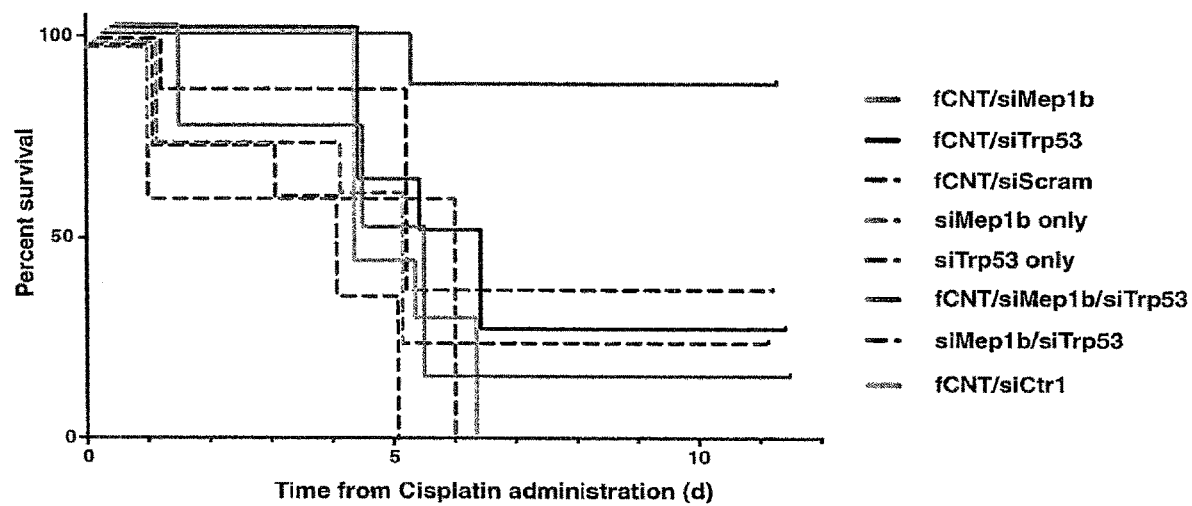
FIGS. 4A-4F show that acute kidney injury (AKI) is mitigated with renal-targeted f-CNT-interference and improved progression-free survival after a cisplatin-induced injury.

Simultaneously Targeting p53 and Meprin-β Reduced Injury and Reduced Fibrosis and Immune Infiltration Fibrillar nanocarbon-mediated RNAi treatment successfully minimized renal injury from a nephrotoxic cisplatin dose and improved progression-free survival. Meprin-1β and p53 were targeted in the PTC and treatment (or control) was administered over 5d (daily doses were 1.6 mg f-CNT±0.087 mg siRNA per kg). The nephrotoxic insult was a single dose of cisplatin (10 mg/Kg) on day 3. Mice were grouped as follows: PBS vehicle; f-CNT/siMep1b; f-CNT/siTrp53; f-CNT/siScram; siMep1b; siTrp53; a combination of f-CNT/siMep1b/siTrp53; and a combination of siMep1b/siTrp53. Progression-free survival was analyzed using the Kaplan-Meier method to score outcomes (FIG. 4A) and kidneys were histologically examined. The cisplatin dose was selected based on a dose response study.

The f-CNT/siMep1b/siTrp53 combination resulted in statistically significant prophylaxis when compared to f-CNT/siMep1b ($P=0.0023$); f-CNT/siTrp53 ($P=0.0142$); f-CNT/siScram ($P=0.0423$); siMep1b alone ($P=0.0110$); siTrp53 alone ($P=0.0003$); or a combination of the siMep1b and siTrp53 ($P=0.0025$). Median times to injury and the complete results of statistical analyses are reported in Table 1.

TABLE 1

Progression-free survival data from the Kaplan-Meier analysis.

| Group | Median time to injury (d) | P values and significance[1] | Hazard ratio and 95% confidence interval[2] |
|---|---|---|---|
| | | Comparison with the fCNT/siMeb1b/siTrp53 group | |
| fCNT/siMep1b/siTrp53 | undefined | — | — |
| fCNT/siMep1b | 4.5 | 0.0023 (**) | 11.40 (2.380 ± 54.62) |
| fCNT/siTrp53 | 5.5 | 0.0142 (*) | 7.402 (1.494 ± 36.66) |
| fCNT/siScram | 5.0 | 0.0423 (*) | 6.702 (1.068 ± 42.06) |
| siMep1b | 5.0 | 0.0110 (*) | 8.444 (1.632 ± 43.70) |
| siTrp53 | 4.0 | 0.0003 (***) | 15.96 (3.550 ± 71.72) |
| siMep1b/siTrp53 | 6.0 | 0.0025 (**) | 11.35 (2.478 ± 51.94) |
| siCtr1 | 4.0 | 0.0006 (***) | 17.71 (3.461 ± 90.59) |
| PBS | undefined | 0.4292 (ns) | 0.1969 (0.0035 ± 11.06) |

[1]P values and statistical significance (ns = not significant) from the Mantel-Cox test.
[2]Hazard ratios and 95% confidence intervals from the Mantel-Haenszel test.

Figure 4B:
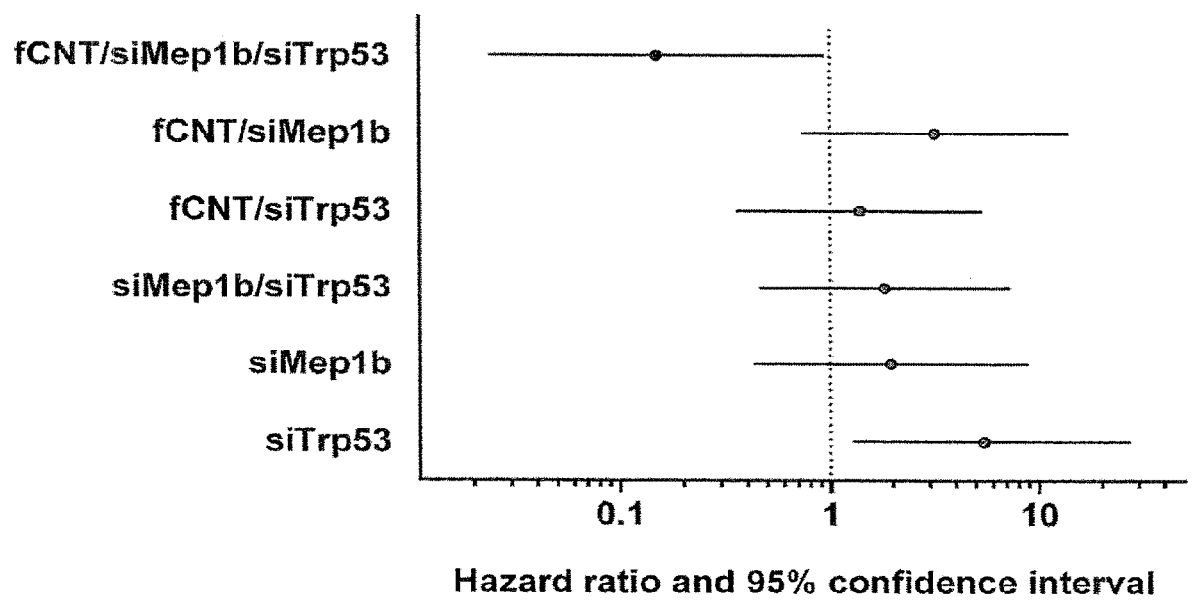

A Forest plot of the hazard ratios strongly favored the f-CNT/siMep1b/siTrp53 combination drug in minimizing renal injury (FIG. 4B). The f-CNT-mediated combination treatment and the vehicle-treated group both had undefined median survival and were not significantly different ($P=0.4292$). There was no advantage in the separate use of f-CNT/siMep1b or f-CNT/siTrp53 and the siRNA vectors alone were ineffective because of degradation and/or low delivery efficiency. The f-CNT/siScram therapy was also ineffective.

Figure 4C:
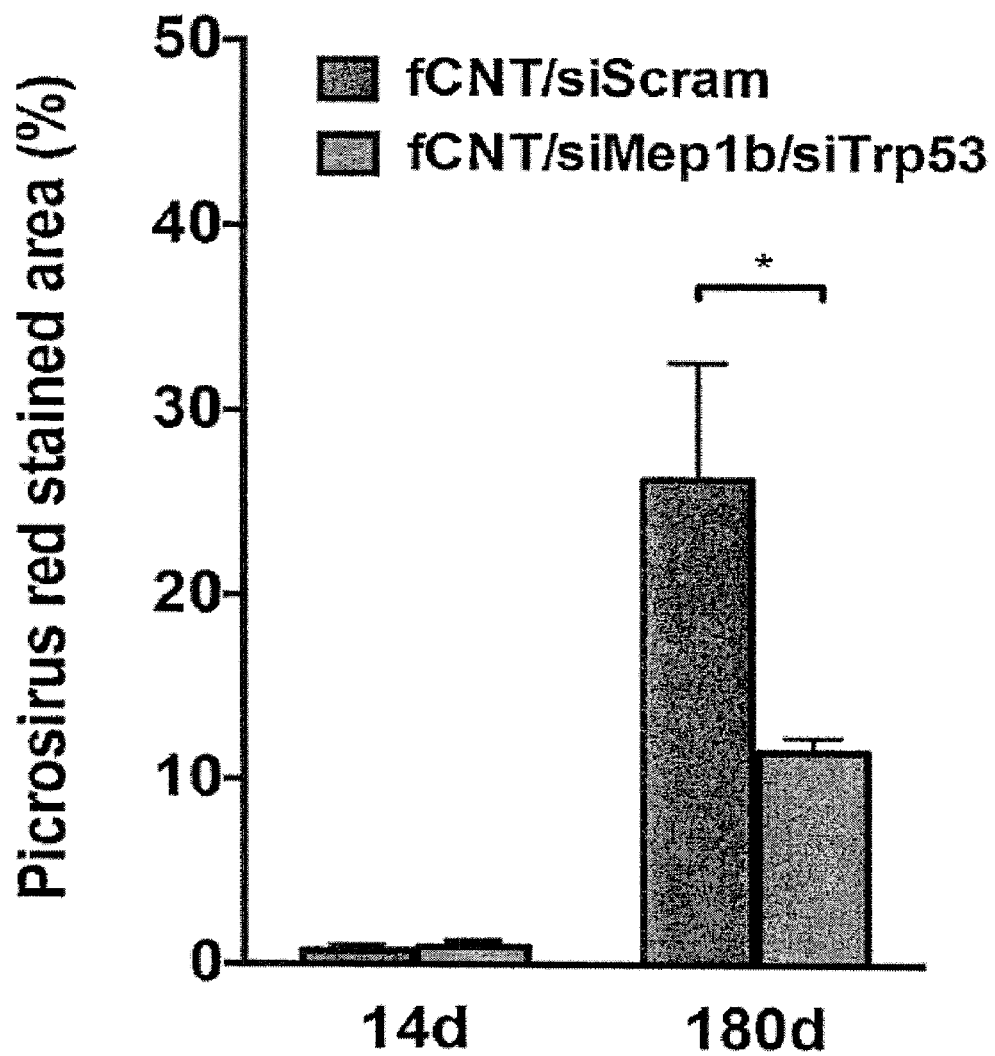

Histological analysis of renal tissue from these mice was performed at 14 days and 180 days post cisplatin injection. Kidney fibrosis is a sign of chronic kidney disease (CKD) and was evaluated via picrosirius red staining) of tissue from f-CNT/siMep1b/siTrp53 and f-CNT/siScram treated animals (FIG. 4C). As expected, there was no difference between the two groups in the early time point, but surprisingly, after 180 days the interstitial fibrotic level was significantly higher for the f-CNT/siScram group ($p=0.0397$), indicating that the treatment decreased fibrosis. This difference was observed in images of kidney sections of mice sacrificed at 180 days post cisplatin injection.

Figure 4D:
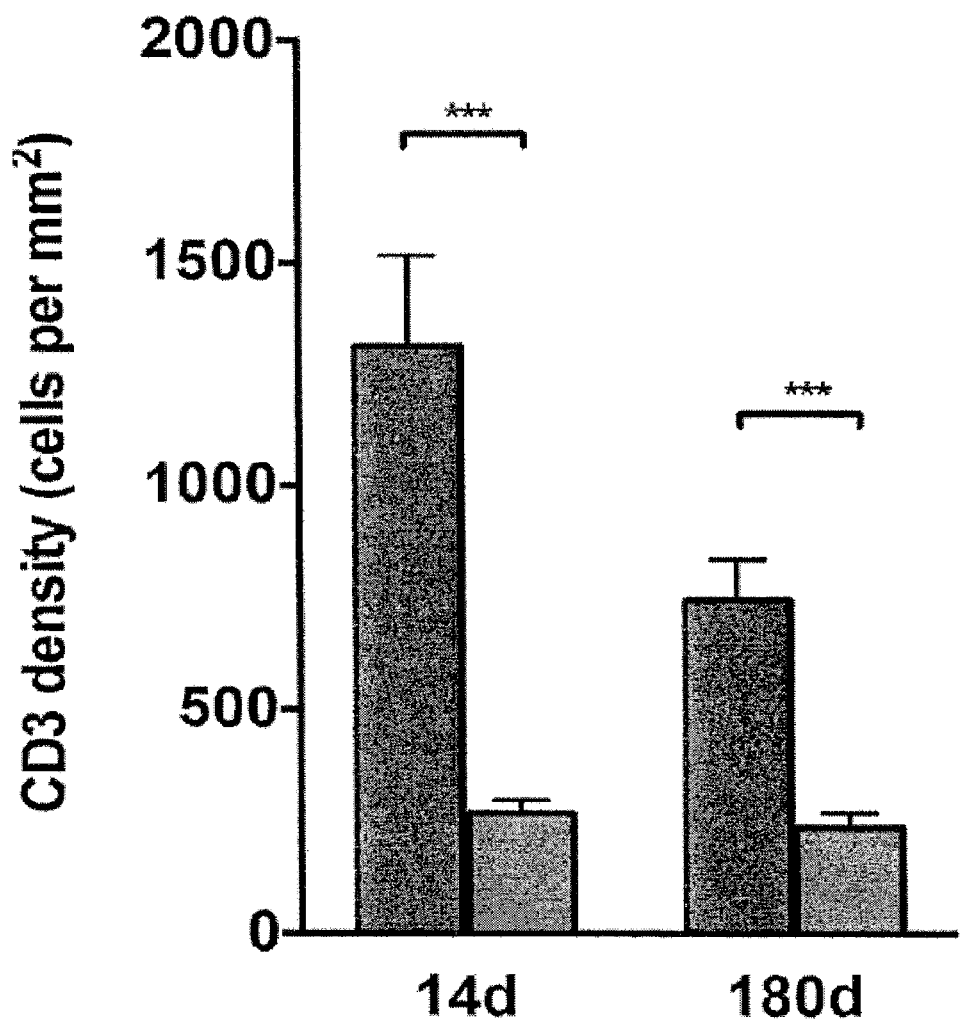
Figure 4E:
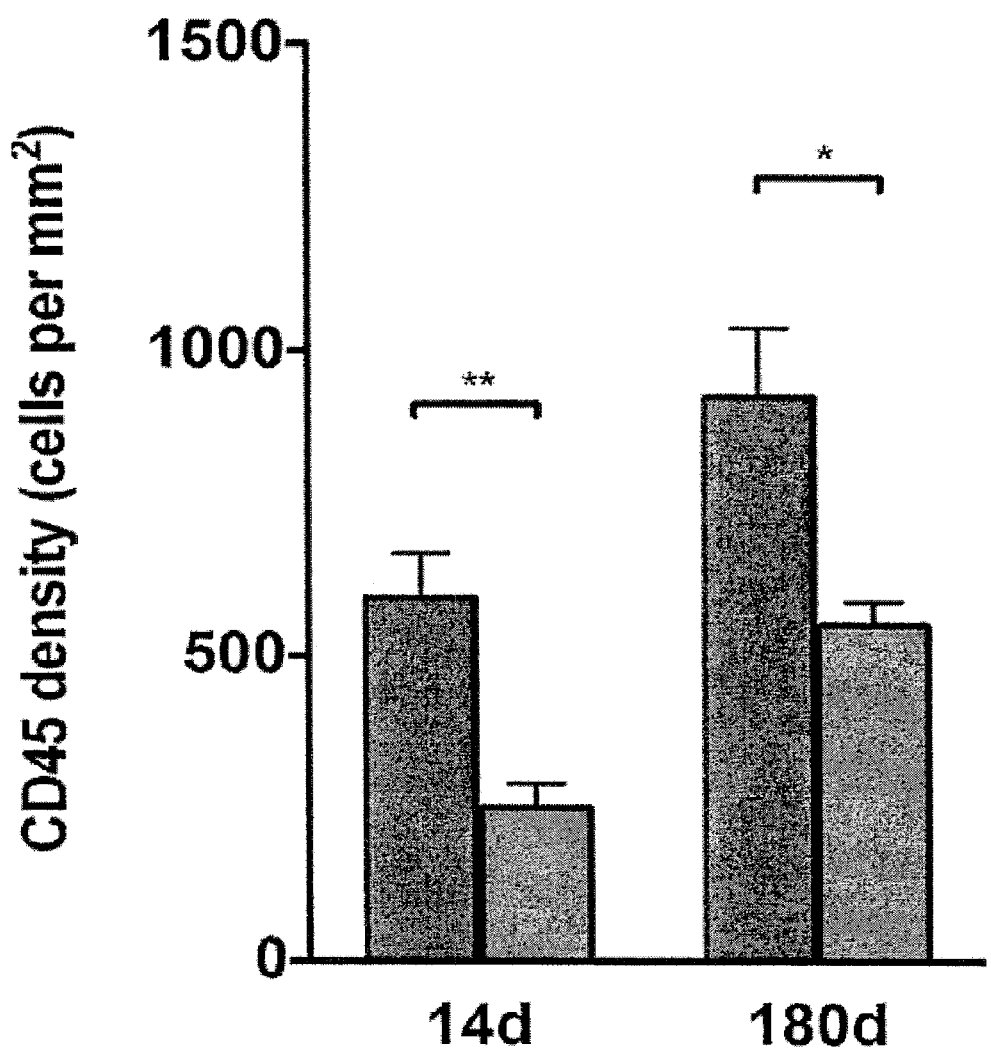
Figure 4F:
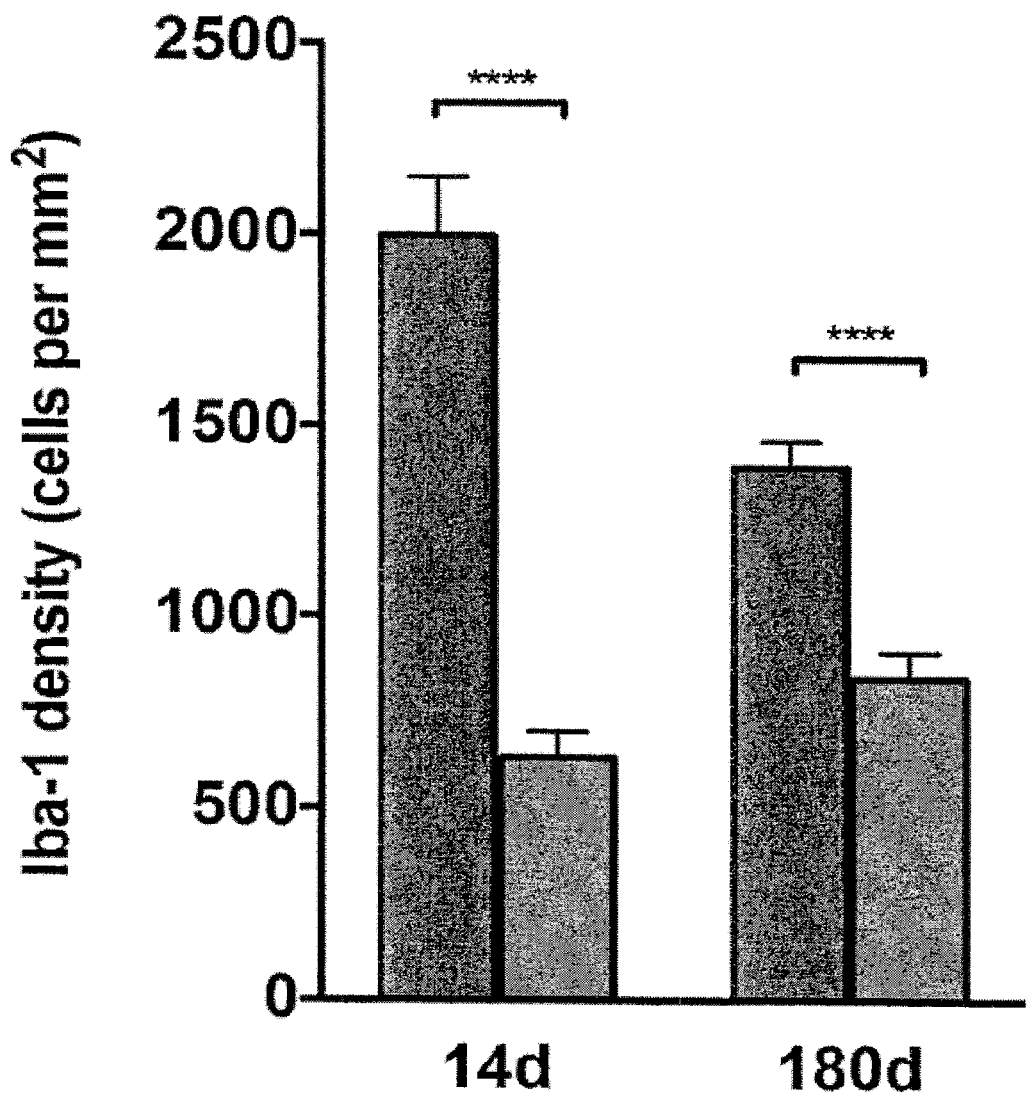

Lymphocyte and macrophage infiltration is recognized to occur in both the early and later phases of cisplatin-induced AKI. Paradoxically, this immune infiltration can aggravate the injury and facilitate repair after the insult. Therefore, immunofluorescence staining for leukocytes, T lymphocytes and macrophages was performed. The quantitative analysis of anti-CD3 antibody staining (FIG. 4D) showed a statistically significant difference between the f-CNT/siScram and f-CNT/siMep1b/siTrp53 group at both early ($p=0.0007$) and later time points ($p=0.0006$). This result indicated that the combination drug was capable of minimizing T cell infiltration after cisplatin treatment. A similar observation was conveyed for anti-CD45 antibody staining of the same tissues, which indicated that lymphocyte infiltration was different within the 2 groups, both at 14 ($p=0.0011$) and at 180 days ($p=0.0100$) (FIG. 4E). In addition, macrophage content within the kidney cortex was also less in the f-CNT/siMep1b/siTrp53 group. Anti-Iba-1 antibody staining of macrophages showed a decrease in macrophage content at both early ($p<0.0001$) and late ($p<0.0001$) time points (FIG. 4F). Renal tissue sections were also assessed using H&E staining and the combination prophylactic drug showed tissue morphology consistent with healthy control mice.

One of ordinary skill will understand that the particular form of RNA used for RNAi in the present invention is not limiting. Activity in treating AKI has also been shown by the survival curve and the weight loss plot for f-CNT that deliver precursor miRNA, mature miRNA (single strand) and mature miRNA (double strand). One of ordinary skill will also understand that compositions and methods of the present application in certain embodiments may also include use of DNA in conjunction with f-CNTs (Alidori, et al., The journal of physical chemistry. C, Nanomaterials and interfaces 117, 5982-5992 (2013)). The compositions and methods of the present application may include the use of any synthetic or modified RNA or DNA. One of ordinary skill will understand that the compositions and methods disclosed herein are applicable in any disease or cancer where RNAi can be used as a therapeutic, but needs to be delivered using a SWCNT, MWCNT or fibrillar macromolecular vehicle.

The foregoing descriptions of specific embodiments of the present application have been presented for purposes of illustration and description. They are not intended to be exhaustive or to limit the application and method of use to the precise forms disclosed. Obviously many modifications and variations are possible in light of the above teaching. It is understood that various omissions or substitutions of equivalents are contemplated as circumstance may suggest or render expedient, but is intended to cover the application or implementation without departing from the spirit or scope of the claims of the present application.

The invention claimed is:

1. A method for preventing or reducing kidney injury in a subject, the method comprising administering to a subject in need thereof an effective amount of a pharmaceutical composition for preventing or reducing kidney injury, the pharmaceutical composition comprising (1) siRNAs non-covalently conjugated to functionalized single walled carbon nanotubes (f-SWCNTs) and (2) a pharmaceutically acceptable carrier, wherein said siRNAs inhibit expression of MEP1B and p53 genes.

2. The method of claim 1, wherein said kidney injury includes injuries caused by one or more of nephrotoxins and ischemia.

3. The method of claim 1, wherein said kidney injury is acute kidney injury.

4. The method of claim 1, wherein the pharmaceutical composition is prophylactically administered before the occurrence of kidney injury.

5. The method of claim 1, wherein the pharmaceutical composition is administered after the occurrence of kidney injury.

6. A method for reducing acute kidney injury in a subject, the method comprising administering to the subject an effective amount of a pharmaceutical composition for reducing acute kidney injury, the pharmaceutical composition comprising: (1) siRNAs non-covalently conjugated to functionalized single wall carbon nanotubes (f-SWCNTs); and (2) a pharmaceutically acceptable carrier, wherein the siRNAs inhibit expression of one or more genes selected from the group consisting of MEP1B and p53 genes.

* * * * *